(12) United States Patent
Carpentier et al.

(10) Patent No.: US 8,764,821 B2
(45) Date of Patent: Jul. 1, 2014

(54) DEGENERATIVE VAVLULAR DISEASE SPECIFIC ANNULOPLASTY RING SETS

(75) Inventors: Alain F. Carpentier, Paris (FR); David H. Adams, New York, NY (US); W. Vaso Adzich, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/422,706

(22) Filed: Mar. 16, 2012

(65) Prior Publication Data

US 2012/0215304 A1 Aug. 23, 2012

Related U.S. Application Data

(60) Continuation of application No. 12/857,113, filed on Aug. 16, 2010, and a division of application No. 12/209,148, filed on Sep. 11, 2008, now Pat. No. 7,959,673, and a continuation-in-part of application No. 12/028,714, filed on Feb. 8, 2008, now abandoned.

(60) Provisional application No. 60/889,178, filed on Feb. 9, 2007.

(51) Int. Cl.
    *A61F 2/24* (2006.01)
(52) U.S. Cl.
    USPC ............................................... 623/2.36
(58) Field of Classification Search
    USPC ............................................... 623/2.36
    See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,164,046 A | 8/1979 | Cooley |
| 4,217,665 A | 8/1980 | Bex et al. |
| 4,275,469 A | 6/1981 | Gabbay |

(Continued)

FOREIGN PATENT DOCUMENTS

| | | |
|---|---|---|
| EP | 0338994 A1 | 10/1989 |
| EP | 0595791 A2 | 5/1994 |

(Continued)

OTHER PUBLICATIONS

Adams, David, et al., "Large Annuloplasty Rings Facilitate Mitral Valve Repair in Barlow's Disease," Society of Thoracic Surgeons 42.sup.ndAnnual Meeting, Jan. 30-Feb. 1, 2006.

(Continued)

*Primary Examiner* — David Isabella
*Assistant Examiner* — Jacqueline Woznicki
(74) *Attorney, Agent, or Firm* — AnneMarie Kaiser; Guy Cumberbatch

(57) ABSTRACT

Annuloplasty rings optimally sized to take into account more of the common degenerative valve pathologies. Each ring has a structural ring body with a shape that complies with predicted shapes of degenerative valvular diseases. The predicted shapes are obtained through careful echocardiographic and intraoperative measurements, and often differ for different annulus orifice sizes. For instance, in mitral rings the larger rings have larger minor axis and oblique axis dimensions relative to their major axis dimensions, and are more circular as opposed to D-shaped. The rings may also be three-dimensional and the relative heights around the rings may change for different sized rings. A mitral ring may have a higher anterior saddle relative to a posterior saddle, with the relative heights varying across the ring sizes. The ring may have varying flexibility around the ring periphery which also changes for different ring sizes.

27 Claims, 15 Drawing Sheets

(56) References Cited

U.S. PATENT DOCUMENTS

| | | |
|---|---|---|
| 4,602,911 A | 7/1986 | Ahmadi et al. |
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,361,190 B2 | 4/2008 | Shaoulian et al. |
| 7,527,647 B2 | 5/2009 | Spence |
| 7,608,103 B2 | 10/2009 | McCarthy |
| 7,959,673 B2 | 6/2011 | Carpentier et al. |
| 7,993,395 B2 | 8/2011 | Vanermen et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |

(56) References Cited

U.S. PATENT DOCUMENTS

| | | |
|---|---|---|
| 2006/0129236 A1 | 6/2006 | McCarthy |
| 2006/0149368 A1 | 7/2006 | Spence |
| 2006/0195183 A1 | 8/2006 | Navia et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0287303 A1 | 11/2009 | Carpentier |

FOREIGN PATENT DOCUMENTS

| | | |
|---|---|---|
| EP | 0860151 A1 | 8/1998 |
| EP | 1034753 A1 | 9/2000 |
| FR | 2708458 A1 | 2/1995 |
| WO | 9119456 A1 | 12/1991 |
| WO | 9503757 | 2/1995 |
| WO | 9640006 A1 | 12/1996 |
| WO | 9741801 A1 | 11/1997 |
| WO | 9742871 A1 | 11/1997 |
| WO | 9806329 A1 | 2/1998 |
| WO | 99/11201 A2 | 3/1999 |
| WO | 9951169 A1 | 10/1999 |
| WO | 9965423 A1 | 12/1999 |
| WO | 0032105 A1 | 6/2000 |
| WO | 01/19292 A1 | 3/2001 |
| WO | 01/26586 A1 | 4/2001 |
| WO | 0147438 A1 | 7/2001 |
| WO | 0187191 A1 | 11/2001 |
| WO | 0203892 A1 | 1/2002 |
| WO | 03020178 A1 | 3/2003 |
| WO | 03041617 A1 | 5/2003 |
| WO | 2004/004607 A1 | 1/2004 |
| WO | 2005/004753 A1 | 1/2005 |
| WO | 2005/034813 A2 | 4/2005 |
| WO | 2005/082278 A2 | 9/2005 |
| WO | 2005/110290 A1 | 11/2005 |
| WO | 2006/041877 A2 | 4/2006 |
| WO | 2006/133186 A2 | 12/2006 |
| WO | 2007-050506 A1 | 5/2007 |
| WO | 2007/100408 A2 | 9/2007 |
| WO | 2007/131513 A1 | 11/2007 |
| WO | 2008/058940 A1 | 5/2008 |
| WO | 2008/063537 A2 | 5/2008 |
| WO | 2008/094469 A2 | 8/2008 |
| WO | 2008/098226 A1 | 8/2008 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al. Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association . COPYRGT.2005; ISSN: 1524-4539.

Type I

Type II

Type IIIa

Type IIIb

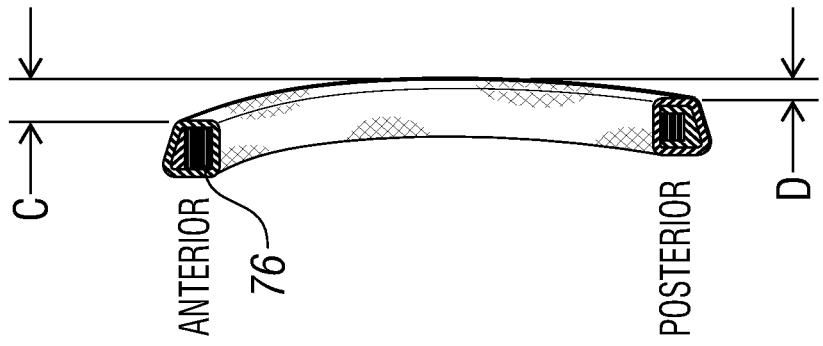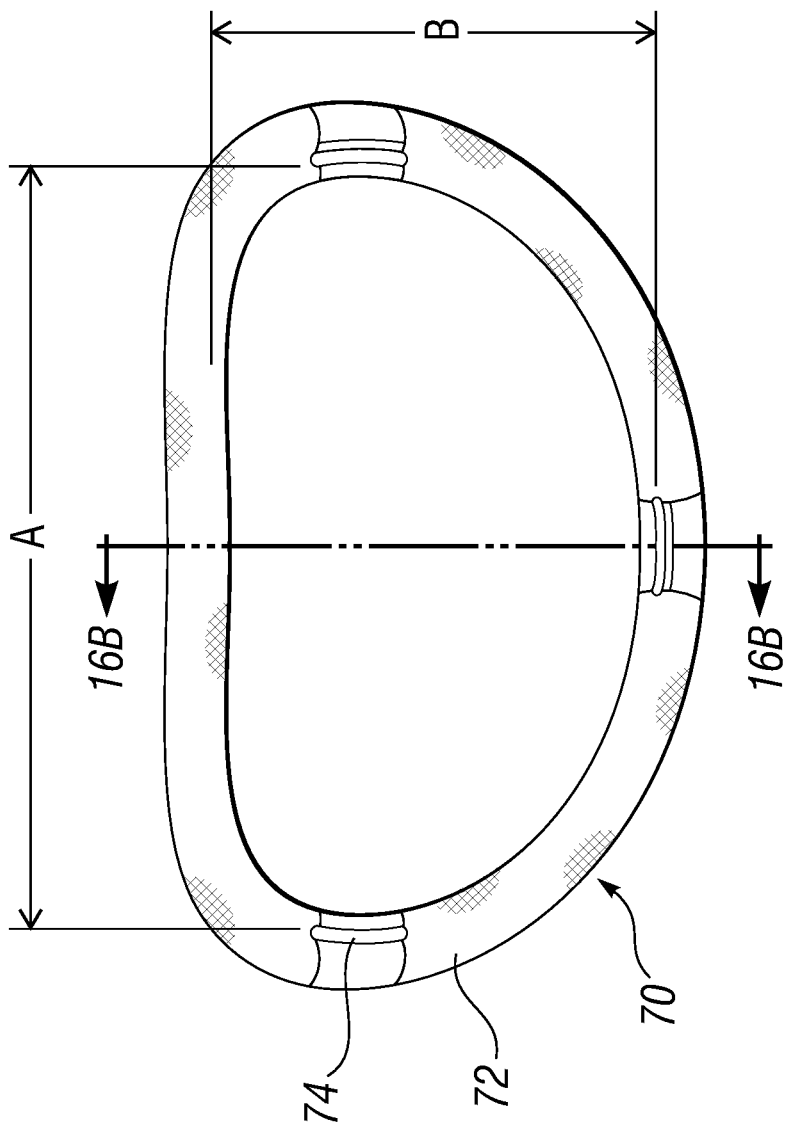

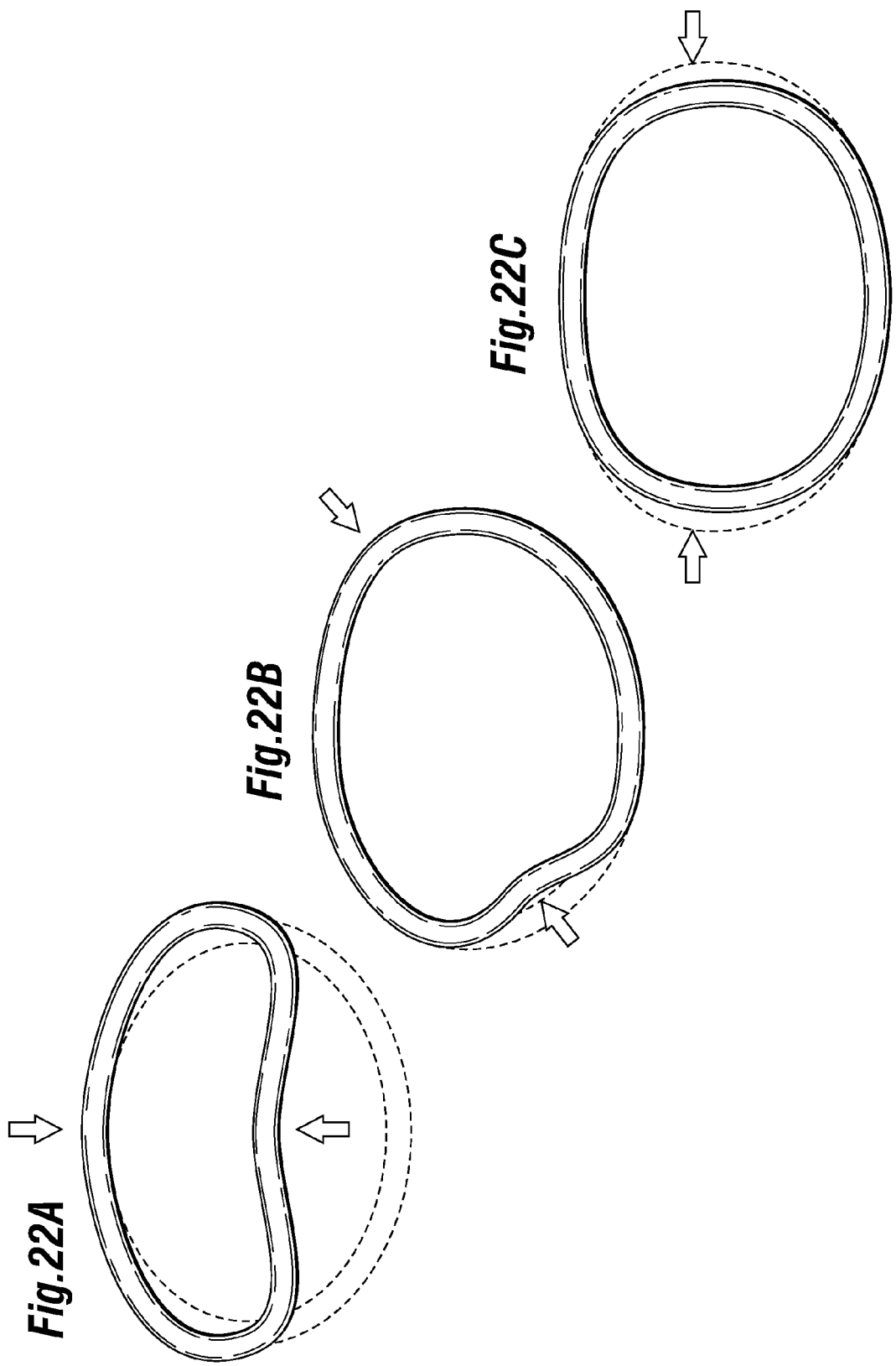

DEGENERATIVE VAVLULAR DISEASE SPECIFIC ANNULOPLASTY RING SETS

RELATED APPLICATIONS

The present application is a continuation of U.S. application Ser. No. 12/857,113, filed Aug. 16, 2010, which is a divisional of U.S. application Ser. No. 12/209,148, filed Sep. 11, 2008, now U.S. Pat. No. 7,959,673, which is a continuation-in-part of U.S. application Ser. No. 12/028,714, filed Feb. 8, 2008, now abandoned, which in turn claims priority under 35 U.S.C. §119(e) to U.S. Provisional Application No. 60/889,178, filed Feb. 9, 2007.

FIELD OF THE INVENTION

The present invention relates to medical devices that support and surgically correct a heart valve experiencing valve regurgitation due to degenerative valvular disease. In particular, the present invention pertains to annuloplasty ring prostheses, in a set of rings, the shape of which is specifically adapted to the anatomical configuration of various forms of degenerative mitral valve disease.

BACKGROUND OF THE INVENTION

The human heart has four valves; the aortic valve, the mitral valve, the pulmonary valve and the tricuspid valve. Various diseases and certain genetic defects of the heart valves can impair their proper functioning. The common defects and diseases affecting each of these valves, and the treatments thereof, are typically different.

As seen in FIGS. 1 and 2, the mitral valve is a two-leaflet (or bicuspid) structure of connective tissue separating the left atrium (LA) from the left ventricle (LV). The mitral valve functions to maintain blood flow in one direction, i.e., from the atrium toward the ventricle during ventricular relaxation or diastole, while preventing back flow in the opposite direction during ventricular contraction or systole. The bases of the two valve leaflets are attached to a circular fibrous structure of the heart called the annulus (AN), and their free edges to chordae tendinae arising from the papillary muscles of the left ventricle. An anterior leaflet (AL) is relatively large and attaches to the anterior segment of the annulus, while a posterior leaflet (PL) is smaller but extends further circumferentially and attaches to the posterior segment of the annulus. The posterior leaflet presents three scallops identified as P1, P2, P3, while the corresponding non-scalloped parts of the anterior leaflet are identified as A1, A2, and A3, according to Carpentier's segmentation.

Several diseases can affect the structure and function of the mitral valve. The mitral valve and, less frequently, the tricuspid valve, are prone to deformation and/or dilation of the valve annulus, tearing of the chordae tendineae and leaflet prolapse, which results in valvular insufficiency wherein the valve does not close properly and allows for regurgitation or back flow from the left ventricle into the left atrium. Deformations in the structure or shape of the mitral or tricuspid valve are repairable.

Mitral regurgitation is one of the most common valvular malfunctions in the adult population, and typically involves the elongation or dilation of the posterior two-thirds of the mitral valve annulus, the section corresponding to the posterior leaflet. The most common etiology of systolic mitral regurgitation is myxomatous degeneration, also termed mitral valve prolapse (29% to 70% of cases), which afflicts about 5 to 10 percent of the population in the U.S. Women are affected about twice as often as men. Myxomatous degeneration has been diagnosed as Barlow's syndrome, billowing or ballooning mitral valve, floppy mitral valve, floppy-valve syndrome, prolapsing mitral leaflet syndrome, or systolic click-murmur syndrome. The symptoms include palpitations, chest pain, syncope or dyspnea, and a mid-systolic click (with or without a late systolic murmur of mitral regurgitation). These latter symptoms are typically seen in patients with Barlow's syndrome, where extensive hooding and billowing of both leaflets are the rule. Some forms of mitral valve prolapse seem to be hereditary, though the condition has been associated with Marfan's syndrome, Grave's disease, and other disorders.

Myxomatous degeneration involves weakness in the leaflet structure, leading to thinning of the tissue and loss of coaptation. Barlow's disease is characterized by myxoid degeneration and appears early in life, often before the age of fifty. In Barlow's disease, one or both leaflets of the mitral valve protrude into the left atrium during the systolic phase of ventricular contraction. The valve leaflets are thick with considerable excess tissue, producing an undulating pattern at the free edges of the leaflets. The chordae are thickened, elongated and may be ruptured. Papillary muscles are occasionally elongated. The annulus is dilated and sometimes calcified. Some of these symptoms are present in other pathologies as well and, therefore, the present application will refer to myxoid degeneration, which is the common pathologic feature of the various diagnoses, including Barlow's syndrome.

Other causes of mitral regurgitation include ischemic heart disease with ischemic mitral regurgitation (IMR), dilated cardiomyopathy (in which the term "functional mitral regurgitation" [FMR] is used), rheumatic valve disease, mitral annular calcification, infective endocarditis, fibroelastic deficiency (FED), congenital anomalies, endocardial fibrosis, and collagen-vascular disorders. IMR is a specific subset of FMR, but both are usually associated with morphologically normal mitral leaflets. Thus, the types of valve disease that lead to regurgitation are varied and present vastly differently.

A number of these disease states have been schematically illustrated in FIGS. 4-8 with FIGS. 3A and 3B illustrating a normal mitral valve in plan and schematic sectional views across the anterior and posterior leaflets. FIGS. 4A and 4B show a mitral valve, also in plan and schematic sectional views, where the annulus is dilated and deformed causing mitral regurgitation. FIGS. 5A and 5B illustrate mitral valves with ruptured and elongated chordae, both causing mitral regurgitation. FIGS. 6A and 6B show symptoms of Barlow's disease with excess tissue and irregularly thickened leaflets. Barlow's disease is seen most often in the young population and has a long-lasting evolution before the onset of valve regurgitation. FIGS. 7A and 7B are views of a mitral valve having fibro-elastic deficiency with thinned leaflets and with excess tissue. Fibro-elastic deficiency, first described by Carpentier, is usually seen in more elderly people, and has a short-lasting evolution before valve regurgitation. The anatomical characteristics include a moderately enlarged kidney-shaped valvular orifice without excess leaflet tissue. The leaflet tissue displays a degeneration of the fibro-elastic bundles. Finally, FIGS. 8A and 8B illustrate the morphology of a mitral valve in Marfan's disease with excess and thin tissue and elongated chordae. Marfan's is a genetic disorder seen at any age. It has a long-lasting evolution before the onset of regurgitation. The annulus is severely dilated and deformed, the chordae are elongated, and the leaflets are thin and degenerative.

As is clear from the illustrations of FIGS. 4-8, many conditions lead to regurgitation. At a structural level, four general types of structural changes of the mitral valve apparatus can cause regurgitation: leaflet retraction from fibrosis and calcification, annular dilation, chordal abnormalities (including rupture, elongation, shortening, or apical tethering or "tenting" as seen in FMR and IMR), and possibly papillary muscle dysfunction.

Another approach to characterizing mitral valve disease is Carpentier's functional classification of the types of leaflet and chordal motion associated with mitral regurgitation. This is illustrated in FIGS. 9A-9D, which show anatomical positions during left ventricular systolic contraction when the leaflets of the mitral valve close or coapt. In Type I, FIG. 9A, excess dilatation of the annulus (seen in dashed outline) results in lack of coaptation between otherwise normal leaflets. Type II (seen in FIG. 9B) mitral regurgitation is due to leaflet prolapse or excessive motion because of rupture or elongation of the chordae tendinae. Type III involves restricted or tethered leaflet motion, classed as occurring during diastole Type Ma (FIG. 9C) or during systole Type IIIb (FIG. 9D). Type IIIb (FIG. 9C) is typically seen in patients with ischemic mitral regurgitation. The course of the leaflets during the cardiac cycle is represented by the dotted lines. (Derived from Carpentier A: Cardiac valve surgery: the "French correction." J Thorac Cardiovasc Surg 86: 323, 1983.)

Various surgical techniques may be used to repair diseased or damaged mitral and tricuspid valves. These include but are not limited to annuloplasty (i.e., contracting the valve annulus to restore the proper size and shape of the valve), quadrangular resection of the leaflets (i.e., removing tissue from enlarged or misshapen leaflets), commissurotomy (i.e., cutting the valve commissures to separate the valve leaflets), shortening and transposition of the chordae tendoneae, reattachment of severed chordae tendoneae or papillary muscle tissue, and decalcification of valve and annulus tissue.

In patients with degenerative mitral valve disease, valve repair using mitral valvuloplasty valve reconstruction, remodeling, or annuloplasty has been the standard for surgical correction of mitral regurgitation and has provided good long-term results. A rigid support ring (e.g., Carpentier-Edwards Classic® Annuloplasty Ring), a semi-flexible ring (e.g., Carpentier-Edwards Physio® Annuloplasty Ring), or a flexible curved band (e.g., Cosgrove-Edwards® Annuloplasty System) may be used. Closed rings are typically D- or kidney-shaped and generally exhibit a minor/major axis ratio of about 3:4. Some rings are flat or planar, while others exhibit three-dimensional bows. The rings are sutured to the deformed annulus so as to theoretically restore its normal shape and size and restore apposition of the leaflets. It should be noted that not all physicians agree which ring is appropriate for any one condition.

For illustration of conventional treatment, FIG. 10A is a surgeon's or plan view of a mitral valve having a deformed annulus leading to regurgitation. For decades, a suitable method of correcting such a deformed mitral valve annulus was to implant a prosthetic annuloplasty ring to restore normal apposition of the leaflets. FIG. 10B shows the annulus after implantation of a Carpentier-Edwards Physio® semi-flexible annuloplasty ring, the most frequently used ring in these cases, although a similar correction can be performed using other rings, such as those described in FIGS. 12-14. The aim of a conventional annuloplasty ring (and conventional wisdom) is to restore the shape of the normal mitral annulus, or, in some conditions, to overcorrect the shape by pulling inward a segment of the annulus. Unfortunately, the attachment of an annuloplasty ring sometimes leads to unintended consequences, as explained below.

Despite accepted treatments for correcting mitral regurgitation, there is a need for a simpler and more effective approach that takes into account more of the common pathologies.

SUMMARY OF THE INVENTION

Annuloplasty rings designed to restore the specific morphology and dynamic characteristics of heart valves damaged by various degenerative valvular disease to overcome some of the limitations of currently available rings is described. For instance, despite satisfactory results over the years with the currently available Carpentier-Edwards Physio® ring, rings described here better meet the need for treating degenerative valvular diseases.

The annuloplasty rings will take into account the effects of degenerative valvular diseases over various heart valve sizes and optimize:
 the ring shape and dimensions,
 the saddle shape configuration,
 the ring flexibility,
 the sewing cuff of the ring, and
 the method of ring selection.

For patients suffering from degenerative valvular diseases, the use of currently available rings to either restore the shape of a normal mitral valve annulus, or overcorrect the annular shape by pulling inward a segment of the annulus yields sub-optimal results. It has been discovered that an optimal technique to correct mitral valve dysfunction in degenerative valvular diseases is to restore the peculiar (abnormal) shape of the annulus characteristic of each type of valvular disease. Furthermore, the ratio between the antero-posterior diameter and the transverse diameter in prior rings is not appropriate for the peculiar ring configuration needed in degenerative valvular disease. Annuloplasty rings are designed taking into account such important characteristics as the overall shape of the annulus, the dimensions in the different orientations, and the curvature of the different segments of the annulus. The global morphology of the annulus of a heart valve affected by degenerative valvular diseases is assessed by metrology, imaging techniques, and intra-operative measurements. Mathematical models have been used to design optimal shapes and size characteristics of the ring sets.

A method of implanting an annuloplasty ring described herein therefore includes assessing the characteristic shape of an annulus of a heart valve afflicted by degenerative valvular disease. The "characteristic shape" of such an annulus includes both its size and three-dimensional shape, and may be obtained by direct or indirect measurements of the particular patient, or by a combination of measurements and an understanding of the morphological characteristic of different disease states. The characteristic shape depends, inter alia, on the nature of the valvular disease and the valve size. In general, the shape becomes more circular as the ring size increases, and conversely becomes more kidney-shaped as the ring size decreases. For example, a number of disease states have been schematically illustrated in FIGS. 4-8, representing the most common pathologies of these diseases. The surgeon may also take into account Carpentier's functional classification of the types of leaflet and chordal motion associated with mitral regurgitation, as illustrated in FIGS. 9A-9D. Other sources considered authoritative in describing characteristic shapes of diseased mitral annuluses include A. Carpentier, et al.: *J Thorac Cardiovasc Surg* 79: 338, 1980, and A. Carpentier: *Cardiac valve surgery: the "French correction." J Thorac Cardiovasc Surg* 86: 323, 1983. The surgeon then references the characteristic shape of the annulus of a heart valve for the particular annulus size and degenerative heart valve disease, and selects an annuloplasty ring that corresponds to that annulus size and shape. In other words, rather than trying to constrict the diseased annulus, or otherwise conform the annulus to a "normal" shape, the goal is to fit the ring to the shape of the annulus that is characteristic of the disease that afflicts the valve being treated.

Similarly, it has been discovered that previous annuloplasty rings having a saddle or upward bulge in the anterior sections may not be optimal in the case of degenerative valvular disease. In particular, prior rings can suffer from ring dehiscence at the commissural segments. The saddle shape of ring sets set forth here are, therefore, optimized to conform to specific morphologies and structures of the different degenerative valvular diseases. Again, saddle shape optimization has been obtained from imaging techniques and intra-operative valve analyses. In addition to an increase in the pre-existing upward bow in the anterior section, a posterior bow has been emphasized. The double bow configuration provides a more compliant structure, particularly at the commissures.

A method of implanting an annuloplasty ring at a patient's valve annulus afflicted by a degenerative heart valve disease is disclosed herein. The method includes measuring the size of the valve annulus, and referencing the characteristic shape of the annulus of a heart valve afflicted by the degenerative heart valve disease. An annuloplasty ring is selected having a size and shape that corresponds to the characteristic shape of the degenerative heart valve disease for that annulus size. Finally, the surgeon implants the selected annuloplasty ring at the patient's valve annulus.

In the preceding method, the step of referencing may comprise echocardiographic and intraoperative measurements of the patient's valve annulus. Where the patient's valve annulus is the mitral valve annulus, the measurements typically include transverse diameter, antero-posterior diameter, and at least three oblique dimensions extending from the geometric center of the annulus to the posterior aspect of the annulus. The degenerative heart valve disease may manifest as mitral valve regurgitation.

A method of manufacturing an annuloplasty ring is disclosed herein and comprises first referencing the characteristic shape of the annulus of a heart valve afflicted by a degenerative heart valve disease. Next, an annuloplasty ring is formed with a size and shape that corresponds to the characteristic shape of the annulus. The characteristic shape may be obtained partly by echocardiographic and intraoperative measurements of an afflicted annulus. For instance, where the patient's valve annulus is the mitral valve annulus, the measurements may include transverse diameter, antero-posterior diameter, and at least three oblique dimensions extending from the geometric center of the annulus to the posterior aspect of the annulus. The degenerative heart valve disease may manifest as mitral valve regurgitation.

The present application also describes a mitral annuloplasty ring for correcting a patient's mitral valve annulus afflicted by a degenerative heart valve disease. The ring has a ring body defining a periphery with an anterior segment opposite a posterior segment, and two side segments. The ring body has a size and shape that corresponds to the characteristic shape of the heart valve afflicted by the degenerative heart valve disease for that annulus size. The characteristic shape of the annulus of the heart valve afflicted by the degenerative heart valve disease may be obtained partly by echocardiographic and intraoperative measurements of an afflicted annulus. Where the patient's valve annulus is the mitral valve annulus, the measurements may typically include transverse diameter, antero-posterior diameter, and one or more, preferably three, oblique dimensions extending from the central axis of the annulus to the posterior aspect of the annulus. The degenerative heart valve disease may manifest as mitral valve regurgitation.

In the preceding rings and methods of forming, and where the patient's valve annulus is the mitral valve annulus, the ring typically defines a major axis and a minor axis and may be selected to have a size and shape symmetric about the minor axis that preserves or restores full leaflet mobility to the patient's mitral valve. Preferably, the size and shape of the ring as proposed herein addresses the problems of excess tissue and related valve dysfunction commonly seen in degenerative valvular diseases. In one example, for rings having a size of 34 mm or larger, the size and shape of the ring conforms to the abnormal annulus shape of Barlow's disease, rather than a normal shape.

Where the patient's valve annulus is the mitral valve annulus, the ring typically defines an anterior segment opposite a posterior segment, and two side segments, and may have varying flexibility around its periphery with the posterior segment being more flexible than the anterior segment. In a preferred embodiment, the ring generally defines a D-shape in plan view with a relatively straight anterior segment opposite a curved posterior segment, and for rings having a size of 34 mm or larger the D-shape diminishes and becomes generally more circular. In another embodiment, the ring is three-dimensional with the center of the anterior segment rising to a height C and the center of the posterior segment rising to height D above a common datum plane, wherein the ratio $C/D > 1$, preferably about 3:1

The present application also discloses a mitral annuloplasty ring, or method of forming such a ring, comprising a ring body defining a periphery with an anterior segment opposite a posterior segment, and two side segments, wherein the periphery is defined in plan view by four circular arcs, one for each segment, connected at points of tangency. Preferably, the ring defines a horizontal line segment a1-a2 having a length A along the major axis of the ring. Two of the four circular arcs defining the ring body periphery consist of portions of two congruent circles c2, c3 that include points a1 and a2, respectively, and both have a center along line segment a1-a2 and include a point b1 at the center of line segment a1-a2.

The mitral annuloplasty ring may further define a vertical line segment b1-b2 extending from center point b1 and having a length $B'=(0.3125 \cdot A)$, a vertical line segment b1-b3 opposite b1-b2, wherein the line segment b2-b3 defines the minor axis of the ring and has a length B. A third one of the four circular arcs defining the ring body periphery consists of an arc T1-T4 that is tangent at both ends to the outer circles c2 and c3 and includes point b2, and a fourth one of the four circular arcs defining the ring body periphery consists of an arc T2-T3 that is tangent at both ends to the outer circles c2 and c3 and includes point b3. Desirably, the lengths A and B of the ring body are selected from the groups consisting of:

A is 34 mm, B is about 23.5 mm;
A is 36 mm, B is about 25.5 mm;
A is 38 mm, B is about 27.2 mm; and
A is 40 mm, B is about 28.7 mm.

A mitral annuloplasty ring defined herein has a ring body defining a periphery with an anterior segment opposite a posterior segment, and two side segments. The ring body in plan view defines a major axis A and a minor axis B extending across from the anterior segment to the posterior segment. The dimensional pairs B and A are selected from the groups consisting of:

A is about 34 mm and B is about 23.5 mm;
A is about 36 mm and B is about 25.5 mm;

A is about 38 mm and B is about 27.2 mm; and

A is about 40 mm and B is about 28.7 mm.

In the aforementioned mitral annuloplasty ring, the ratio of B/A is preferably greater than or equal to 0.69 and less than or equal to 0.73. Furthermore, the axial elevation of the anterior segment is preferably higher than the axial elevation of the posterior segment. In one embodiment, the ring body generally defines a D-shape in plan view with a relatively straight anterior segment opposite a curved posterior segment, and as the ring size increases the D-shape diminishes and becomes generally more circular.

Another mitral annuloplasty ring defined herein comprise a ring body defining a periphery with an anterior segment opposite a posterior segment, and two side segments, the ring body in plan view defining a major axis A and a minor axis B extending across from the anterior segment to the posterior segment, wherein A is about 34 mm and B is about 23.5 mm. In a similar ring, A is about 36 mm and B is about 25.5 mm, or A is about 38 mm and B is about 27.2 mm, or A is about 40 mm and B is about 28.7 mm. Desirably, the ring body is also three-dimensional with the center of the anterior segment rising to a height C and the center of the posterior segment rising to height D above a common datum plane, wherein the ratio C/D>1, preferably about 3:1.

Another method of manufacturing mitral annuloplasty rings disclosed herein includes forming mitral annuloplasty rings of different sizes where each ring has a ring body defining a periphery with an anterior segment opposite a posterior segment, and two side segments. Each ring body in plan view defines a major axis dimension A and a minor axis dimension B extending across from the anterior segment to the posterior segment, and each ring has an identified orifice size. The ring bodies in plan view approximate a D-shape for smaller ring sizes and have gradually more circular shapes for larger ring sizes. Desirably, the method includes forming the ring body to be three-dimensional with the center of the anterior segment rising to a height C and the center of the posterior segment rising to height D above a common datum plane, wherein the ratio C/D>1, preferably about 3:1. The shapes of the ring bodies in plan view for different orifice sizes preferably change to comply with predicted shapes of degenerative valvular disease for different annulus orifice sizes. In one example, the ratio B/A for each ring body increases with increasing ring orifice size.

In accordance with another embodiment, ring sets comprise two upward bows on both the anterior and posterior sections of the ring bodies. Desirably, the anterior bow is more pronounced than the posterior bow so as to adapt to the specific configuration of the mitral annulus. For instance, the anterior section may bow upward between 2-8 mm, preferably between 3-6 mm. In one embodiment, the anterior bow in a set of annuloplasty rings changes across ring sizes to take into account the tendency of the annulus of degenerative valves to flatten as the annulus dilates. The posterior bow desirably varies between 0.5-4 mm, and preferably between 0.5-2 mm. Again, the relative posterior bow typically flattens for larger annulus sizes.

The set of annuloplasty rings for correcting a heart valve annulus, comprises a set of rings each having a ring body able to resist deformation when subjected to the stress imparted thereon by the valve annulus. The ring bodies are each arranged around a flow axis having an upward direction and a downward direction, the downward direction corresponding to the direction of blood flow through the valve annulus when the annuloplasty ring is implanted. Each ring has an identified orifice size and the proportional shapes of the ring bodies change with increasing orifice sizes of the rings in the set. The annuloplasty rings may be configured for implantation in various positions, including the mitral and tricuspid positions. The annuloplasty rings are desirably configured for implantation in the mitral position and smaller rings in the set generally define a D-shape in plan view with a relatively straight anterior segment opposite a curved posterior segment, and as the orifice sizes of the rings become larger the D-shape diminishes and becomes generally more circular. Furthermore, the ring bodies are preferably three-dimensional with the center of the anterior segment rising to a height C and the center of the posterior segment rising to height D above a common datum plane, wherein the ratio C/D>1. Preferably, the ratio C/D is about 3:1, and the height C of the anterior segment rises up to at least 6 mm above the common datum plane. In a preferred embodiment the change in proportional shapes of the ring bodies is a change in the ratio of the heights C and D of the opposite sides.

In one particularly useful embodiment, the proportional shapes of the ring bodies change to comply with the characteristic shapes of a particular valvular disease for different annulus orifice sizes. The characteristic shapes of a particular valvular disease may be calculated from echocardiographic and intraoperative measurements. For instance, if the annuloplasty rings are configured for implantation in the mitral position and have an anterior segment opposite a posterior segment, the measurements include transverse diameter, antero-posterior diameter, and at least three oblique dimensions extending from a central axis of the annulus to the posterior aspect of the annulus.

In another aspect, a set of mitral annuloplasty rings each comprises a ring body able to resist deformation when subjected to the stress imparted thereon by the mitral valve annulus and arranged around a flow axis having an upward direction and a downward direction. The downward direction corresponds to the direction of blood flow through the mitral valve annulus when the annuloplasty ring is implanted. In accordance with a preferred embodiment, each ring body defines in plan view a major axis A and a minor axis B extending across from an anterior segment to a posterior segment, and each ring has an identified orifice size. In plan view, as seen along the flow axis, the ring bodies in a set of rings defines different proportional shapes depending on the type of degenerative valvular disease in the size of the ring. The proportional shapes of the ring bodies change with increasing orifice sizes of the rings in the set. For instance, the ratio B/A for each ring body increases with increasing orifice sizes of the rings in the set. In the latter case, the ring bodies will have a more pronounced circular shape in the larger sizes and more pronounced kidney or D-shapes in the smaller sizes. The set of rings is optimally sized to take into account more of the common pathologies. The ring bodies may also have varying flexibility around their peripheries, wherein the relative flexibility between the anterior segment and the posterior segment changes with increasing ring orifice size. Desirably, each ring further includes a suture-permeable covering over the ring body, and the covering has a smooth relatively flat inflow side and a stepped outflow side.

In a still further aspect a set of mitral annuloplasty rings each comprises a ring body able to resist deformation when subjected to the stress imparted thereon by the mitral valve annulus and arranged around a flow axis having an upward direction and a downward direction. The downward direction corresponds to the direction of blood flow through the mitral valve annulus when the annuloplasty ring is implanted. Each ring has an identified orifice size, and each ring body in plan view defines a major axis A and a minor axis B extending across from an anterior segment to a posterior segment, the ratio B/A for the ring bodies changing with increasing ring orifice size. The ring bodies are preferably D-shaped in plan view with a relatively straight anterior segment opposite a curved posterior segment, wherein the shape of the ring bodies is a more pronounced D-shape for smaller rings and becomes gradually more circular with increasing ring orifice size. The ring bodies may also be three-dimensional with the center of the anterior segment rising to a height C and the center of the posterior segment rising to height D above a common datum plane, and wherein the ratio C/D changes with increasing ring orifice size. Desirably, each ring further includes a suture-permeable covering over the ring body, and the covering has a smooth relatively flat inflow side and a stepped outflow side. The ring bodies each define a continuous or discontinuous periphery.

BRIEF DESCRIPTION OF THE DRAWINGS

Features and advantages of the devices and methods disclosed herein can be understood with reference to the specification, claims, and appended drawings wherein:

FIGS. 16A and 16B are plan and posterior sectional views of an exemplary annuloplasty ring;

FIGS. 22A-22C illustrate the effects of application of opposite inward forces across different oblique planes on the exemplary rings;

DETAILED DESCRIPTION OF THE PREFERRED EMBODIMENTS

A novel set of annuloplasty rings for correcting pathologies resulting in mitral regurgitation is provided. In one embodiment, a set of rings is structurally defined by ring bodies wherein the proportional shapes of the ring bodies change with increasing identified orifice sizes of the rings in the set. Each ring includes a ring body and an outer covering of suture-permeable material, typically silicone covered with fabric. The set of rings is formed of ring bodies that will initially resist deformation when subjected to the stress imparted thereon by the mitral valve annulus, i.e. the shapes of the ring bodies are formed during manufacture and are not easily manipulated. Examples include ring bodies formed of titanium or Eligiloy® bands. In the absolute sense, however, even these relatively rigid ring bodies can be deformed with the application of sufficient force. However, a ring that is "able to resist deformation" or is "generally rigid" is not a fully flexible ring. Indeed, in a preferred embodiment the rings described herein do not possess the same degree of flexibility in every cross-plane. A desirable configuration consists of a ring that is more flexible across the antero-posterior dimension (the minor axis) than it in a cross plane transverse to the antero-posterior dimension (the major axis). This preserves the remodeling effect while permitting some flexing in the antero-posterior dimension.

A "set of annuloplasty rings" has a specific meaning of a commercial set of rings that are intentionally manufactured to have differing proportional sizes or shapes. That is, the set of rings would be marketed and/or sold together, and the definition of a set of rings excludes the forcible deformation of an individual ring by a surgeon to change its proportional shape relative to other rings in that particular commercial set. That would not be a "set" of rings with differing proportions, but instead a set of rings of the same proportion that have been sold and modified after the fact. Also, a "set of annuloplasty rings" excludes the random combination of rings of different sizes from different lines or sets of rings. For instance, a set of Carpentier-Edwards Physio® semi-flexible annuloplasty rings described above are available in sizes 24-40 mm from Edwards Lifesciences of Irvine, Calif. Each of these rings has the same size proportions across the commercial set.

Figure 10A:
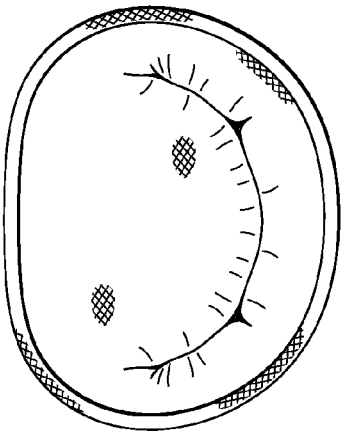
FIG. 10A is a surgeon's or plan view of a mitral valve having a deformed annulus leading to regurgitation.
Figure 10B:
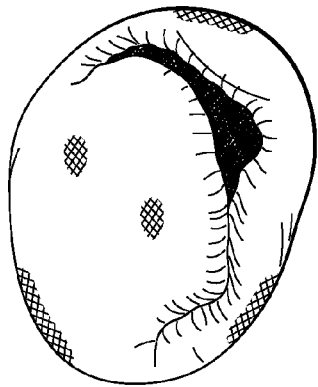
FIG. 10B shows correction of the deformed mitral valve annulus using a suitable prosthetic annuloplasty ring of the prior art to restore normal apposition of the leaflets.
Figure 11A:
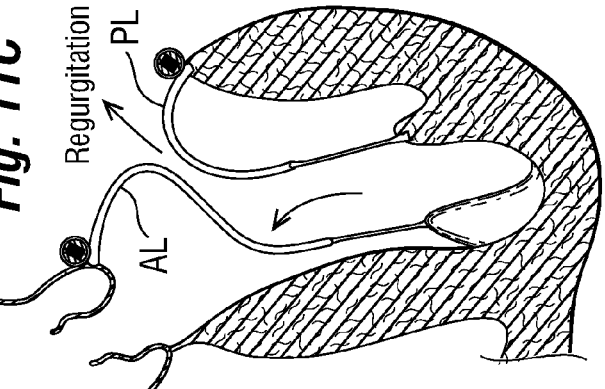
FIGS. 11A-11C are schematic sectional views of a mitral valve corrected with an annuloplasty ring of the prior art as shown in FIG. 10B through the diastolic/systolic phases and showing regurgitation resulting from systolic anterior motion (SAM) of the anterior leaflet due to excess tissue.
Figure 11B:
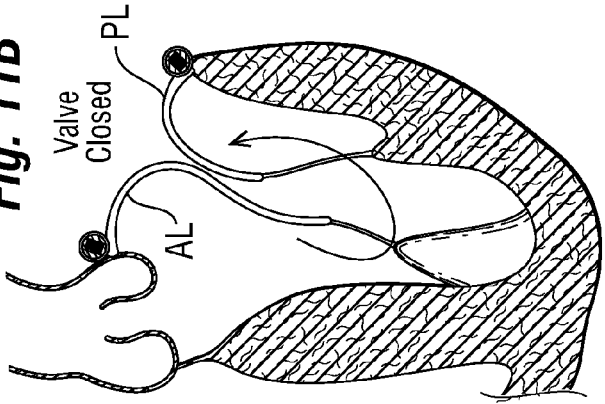
Figure 11C:
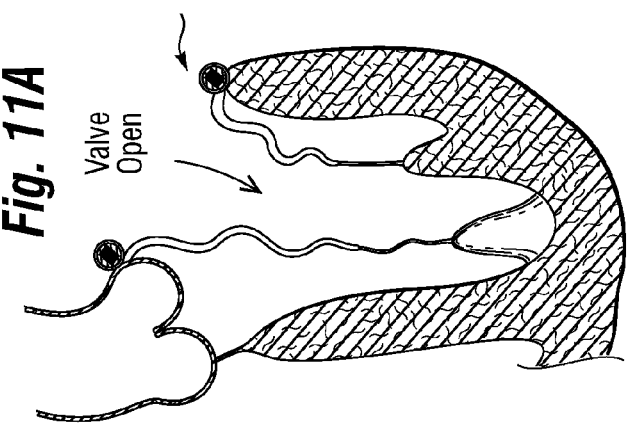

FIGS. 11A-11C are schematic sectional views of a mitral valve corrected with an annuloplasty ring of the prior art, such as a Carpentier-Edwards Physio® semi-flexible annuloplasty ring shown in FIG. 10B. FIG. 11A shows the diastolic phase in the left ventricle expands to pull blood in through the mitral valve. FIG. 11B illustrates the positions of the anterior leaflet (AL) and posterior leaflet (PL) at the initiation of the systolic phase when the left ventricle contracts to force blood through the aortic valve. Because of Systolic Anterior Motion (SAM), and because excess tissue of the posterior leaflet (PL) pushes the anterior leaflet (AL) toward the left ventricular outflow tract, leaflet coaptation is impaired causing residual leakage, or regurgitation. Therefore, the ostensible correction of one mitral condition sometimes creates another problem.

Figure 12A:
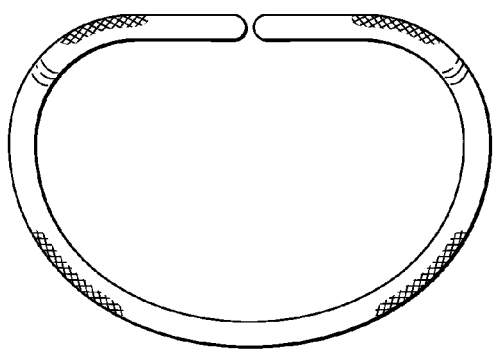
FIGS. 12A and 12B are plan and posterior elevational views, respectively, of a Carpentier-Edwards Classic® annuloplasty ring of the prior art.
Figure 12B:
Figure 13A:
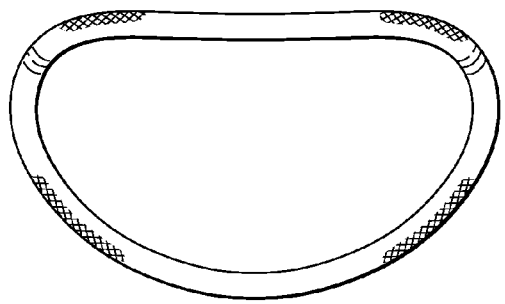
FIGS. 13A and 13B are plan and posterior elevational views, respectively, of a Carpentier-Edwards Physio® annuloplasty ring of the prior art.
Figure 13B:
Figure 14A:
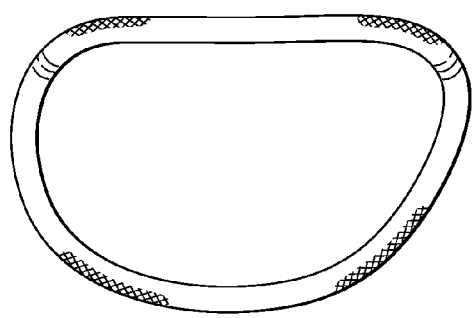
FIGS. 14A and 14B are plan and posterior elevational views, respectively, of a Carpentier-McCarthy-Adams IMR ETlogix® annuloplasty ring of the prior art.
Figure 14B:
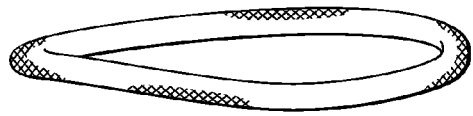

As mentioned above, various annuloplasty rings of the prior art are known for providing the correction to normal mitral annulus shape. For instance, FIGS. 12A and 12B are plan and posterior elevational views, respectively, of a rigid Carpentier-Edwards Classic® annuloplasty ring. FIGS. 13A and 13B show a Carpentier-Edwards Physio® semi-rigid annuloplasty ring. The Physio® ring includes a relatively rigid anterior side and a gradually more flexible posterior side, to provide some flexibility to the ring while preserving its annular remodeling effect. Finally, FIGS. 14A and 14B illustrate a Carpentier-McCarthy-Adams IMR ETlogix® annuloplasty ring, which is relatively rigid around its asymmetric periphery. In all of these and all known annuloplasty rings, the differently sized rings in a set of marketed rings all have the same size and shape proportions, as well as the same relative flexibilities for those types of rings. The present invention is an improvement on these and other annuloplasty ring designs, including those disclosed in U.S. Pat. Nos. 4,055,861 and 5,104,407 both to Lam, Nguyen, and Carpentier, and U.S. Patent Publication No. 2005/0131533 to Carpentier, et al., whose disclosures are expressly incorporated herein.

Figure 15C:
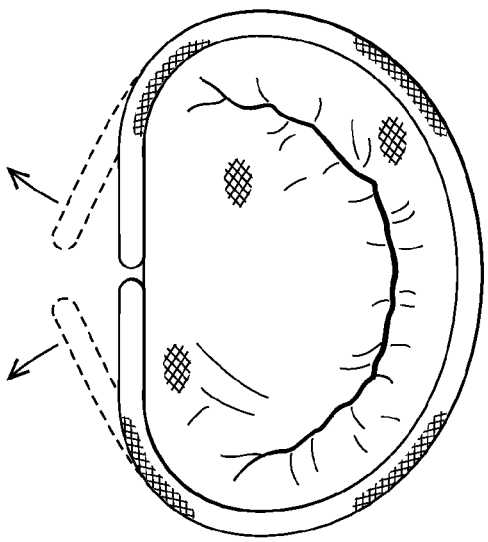
FIGS. 15A-15C are surgeon's views of a mitral valve: 15A) in Barlow's disease displaying excess valvular tissue, 15B) showing an irregular line of leaflet closure and systolic anterior motion (SAM) after correction with a prior art annuloplasty ring, and 15C) after free ends of the prior art annuloplasty ring have been bent outward to restore a desired line of leaflet coaptation.
Figure 15B:
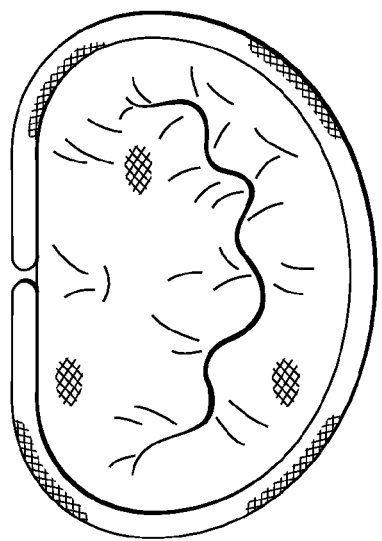
Figure 15A:
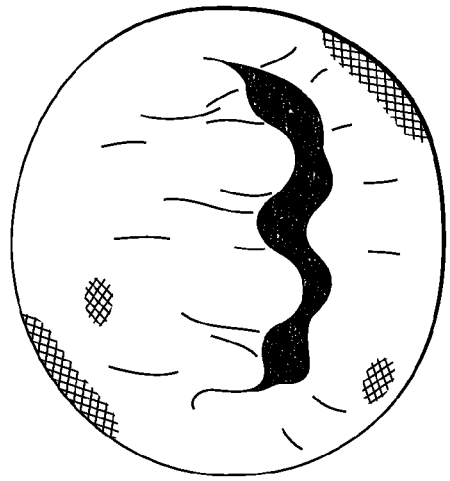

In some instances, annuloplasty rings of the prior art can be modified or bent to lessen some of the side-effects described above. FIGS. 15A-15C are surgeon's views of a mitral valve having symptoms of Barlow's disease treated with an open Carpentier-Edwards Classic® annuloplasty ring. One observed result is systolic anterior motion (SAM), as seen in FIG. 15B. The inventor has proposed that in some cases bending the free ends of the annuloplasty ring outwards, as seen in FIG. 15C, restores normal apposition of the leaflets. Although this technique is sometimes very effective, it is difficult to predict and requires subjective judgment about how far to bend the ends of the ring. Also, bending the ring may diminish the strength of the device. Furthermore, some rings form continuous peripheries and are not as simple to bend.

Mitral valves remain competent (non-regurgitant) for a long time despite a severely abnormal valve morphology and structure, including with symptoms of Barlow's disease which creates the most pronounced abnormal valve morphology. Valve regurgitation occurs only when a leaflet dysfunction develops, as categorized by Carpentier in the literature, and as described above with reference to FIGS. 9A-9D. Also, as mentioned above, attempts to restore the "normal" annulus shape may not improve regurgitation. The inventor has discovered that an efficient valve reconstruction for degenerative valvular diseases involves restoring the peculiar anatomy of the annulus rather than imposing a normal shape thereto. Stated another way, the shapes of the rings in any set of rings in accordance with the present invention conform to the shape of the diseased but well-functioning valves. A degenerative dysfunction should be corrected by restoring the peculiar configuration of the degenerative valve, and not an anatomically "normal" (or non-diseased) configuration.

The present invention therefore encompasses specifically-shaped rings to conform to abnormal mitral annuluses. The particular shapes of the abnormal annuluses can be obtained from morphometric studies by echocardiography, magnetic resonance imaging (MRI), ultrasound, and direct physical measurements in the operating room. Numerous careful measurements that may be vetted with statistical analysis provide the surgeon with definitions of annulus shape for different degenerative valvular diseases, and for different annulus sizes. Indeed, another aspect recognized by the present inventor is that the annuluses of different sized patients often present differently for the same degenerative valvular disease. The goal in creating specific ring shapes for all the anticipated sizes is to remodel the annulus and restore leaflet co-optation without creating SAM. As explained above, it has been found that, contrary to other diseases, a ring annuloplasty for degenerative valvular disease should restore not the shape of a normal mitral annulus, but the annular shape specific of each type of degenerative valve. One goal of the rings defines herein is to select a mitral annuloplasty ring with a long or major axis and a short or minor axis to have a size and shape symmetric about the minor axis and that preserves or restores full leaflet mobility. The size and shape of the annuloplasty ring desirably addresses the problems of excess tissue and related valve dysfunction commonly seen in degenerative valvular diseases.

The present invention therefore contemplates a set of rings of different identified or labeled sizes each having a structural ring body able to resist deformation when subjected to the stress imparted thereon by the mitral valve annulus. Each ring body is arranged around a flow axis having an upward direction and a downward direction, the downward direction corresponding to the direction of blood flow through the valve annulus when the annuloplasty ring is implanted. For different orifice sizes, the proportional shapes of the ring bodies in the set change, depending on the particular degenerative valvular disease at issue. By predicting the shape of the mitral annulus for that disease and that annulus size, a set of rings that will match most patients can therefore be provided. Exemplary ring shapes are shown and described below.

FIGS. 16A and 16B are plan and section views of an exemplary annuloplasty ring 70 of the present invention. The ring 70 is shown with a fabric covering 72 over a structural interior support or body 74. Typically a suture-permeable interface 76 fills the space between the covering 72 and interior body 74.

As seen in FIG. 16A, the annuloplasty ring 70 of the present invention can be described as having a closed or continuous periphery with an anterior (top) section, a posterior (bottom) section and right and left sides therebetween. Preferably, all of the sides are generally curvilinear with no specific demarcations to indicate abrupt transitions therebetween. Rather, smooth transitional sections between the adjacent sides provide curvilinear connections that give the ring a generally rounded (e.g., oval) configuration, or more preferably a somewhat D- or kidney-shaped configuration with a relatively straight anterior segment opposite a curved posterior segment. The kidney-shaped configuration more accurately mimics the mitral annulus. It should be understood, however, that the aspect of the invention wherein a set of rings is optimally sized, and more specifically, where the proportional shapes or characteristics of each ring changes with the annulus size, may be beneficial to rings of other shapes and configurations. For instance, changing proportional shapes for different sized rings may be useful for asymmetric rings, three-dimensional rings, discontinuous (C-shaped) rings, tricuspid or ovoid-shaped rings, etc. The present invention thus generally provides optimally sized annuloplasty ring sets, though the illustrated application is mitral valve correction.

The exemplary ring 70 in the plan view of FIG. 16A has a minor axis dimension B and a major axis dimension A, and is three-dimensional. FIG. 16B shows preferred heights above a datum plane, with the center of the anterior segment rising to a height C and the center of the posterior segment rising to a height D, with a desired ratio of C/D>1. The preferred ratio of C/D is about 3:1, with the smallest rings rising to a height C of about 3 mm on the anterior side and the largest to about 6 mm, potentially up to 8 mm. The height D on the posterior side rises to about 2 mm, potentially up to 3 mm.

Table I below indicates exemplary values of the heights above a datum plane of the anterior segment C and the center of the posterior segment D of an exemplary ring 70. These magnitudes may vary by ±20%, while maintaining the approximate relative sizes across the ring set.

TABLE I

| Labeled ring size (mm) | Anterior Height, C (mm) | Posterior Height, D (mm) |
|---|---|---|
| 24 | 3.0 | 1.0 |
| 26 | 3.3 | 1.0 |
| 28 | 3.6 | 1.2 |
| 30 | 4.0 | 1.2 |
| 32 | 4.4 | 1.4 |
| 34 | 4.8 | 1.4 |
| 36 | 5.2 | 1.6 |
| 38 | 5.6 | 1.8 |
| 40 | 6.0 | 2.0 |

It should be noted that the ratio of the heights of the opposite sides, anterior and posterior, changes with increasing orifice size. The smallest ring, 24 mm, has a C/D ratio of 3.0/1.0, or about 3.0, while a mid-size ring, 34 mm, has a C/D ratio of 4.8/1.4, or about 3.4. The C/D ratio thus varies as the ring size increases. Although this ratio change may appear slight, the inventors contemplate more significant C/D ratio changes for certain degenerative conditions. The trend may be such that the larger rings have a greater or lesser C/D ratio than smaller rings, or in other words the anterior height relative to the posterior height becomes greater or lesser in larger rings. Therefore, not only can the proportional plan view shape of the rings change, but the three-dimensional shape of the rings can also change.

Two general formulas for anterior and posterior heights are given below for the exemplary ring sets, though those of skill in the art will see that not all rings heights in Table I comport with these formulas. Therefore, they should be viewed as guides only.

$$C=(A-10)/5$$

$$D=(C-2)/2$$

The interior body 74 is desirably made of material(s) that are "generally rigid" and will initially resist deformation when subjected to the stress imparted thereon by the mitral valve annulus of an operating human heart. In this sense, "deformation" means substantial permanent deformation from a predetermined or manufactured shape; the opposite concept of which is "elastic" meaning the ability to recover the ring shape in the absence of an external force. A number of "generally rigid" materials can be utilized that will perform this function, including various bio-compatible polymers and metals and/or alloys. Certain polyesters that resist deformation and also rapid degradation within the body may be used (a material that degrades slowly may provide the required initial support). In a preferred embodiment, at least an inner core or body of the annuloplasty ring of the present invention is made of a suitable metal, such as titanium or its alloys, or ELGILOY made by Elgiloy, L.P. of Elgin, Ill., U.S.A. The core or ring body may be one piece, or may include a plurality of concentric or otherwise cooperating elements.

The interface 76 is a molded silicone tube or band around the ring body 74 and the fabric covering on the exterior of the ring is desirably Dacron (polyethylene terephthalate). The tubular fabric covering around the silicone sleeve provide an interface for securing the annuloplasty ring to the mitral annulus, although other interfaces are contemplated. For example, rings having outward hooks or barbs are known in the art.

Figure 1:
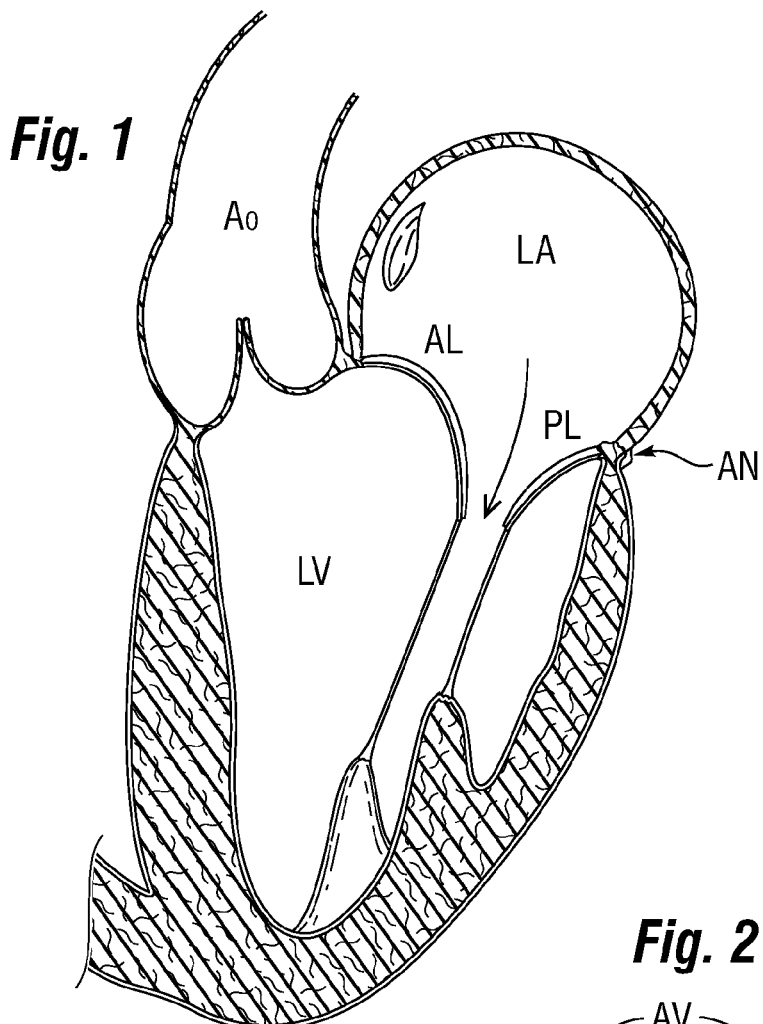
FIG. 1 is a cross-sectional view of the left side of the human heart showing the left atrium (LA) separated from the aorta (Ao) by the mitral valve.
Figure 2:
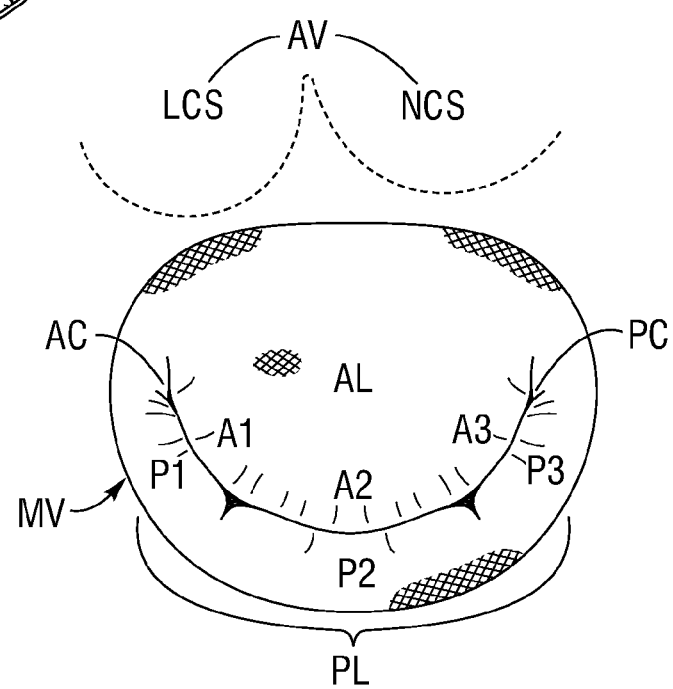
FIG. 2 is a surgeon's or plan view of a normal mitral valve in the closed position illustrating the anterior leaflet (AL) and the posterior leaflet (PL) attached to the annulus (AN), and indicating eight identifiable leaflet segments.
Figure 3A:
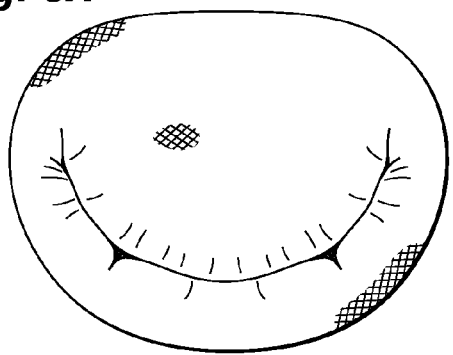
FIGS. 3A and 3B illustrate a normal mitral valve in plan and schematic sectional views across the anterior and posterior leaflets.
Figure 3B:
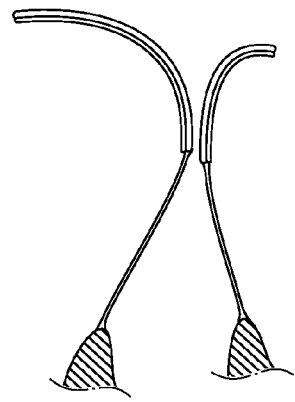
Figure 4A:
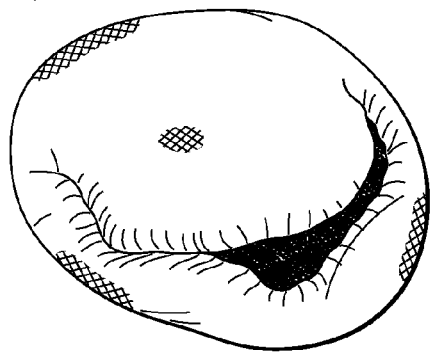
FIGS. 4A and 4B show a mitral valve in plan and schematic sectional views where the annulus is dilated and deformed causing mitral regurgitation.
Figure 4B:
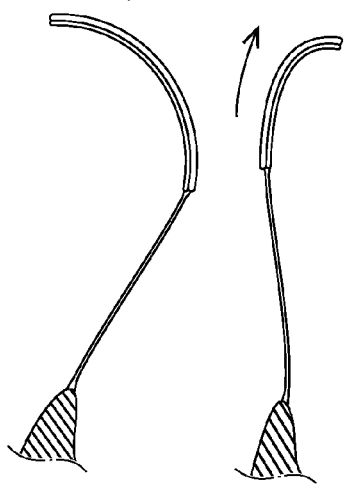
Figure 5A:
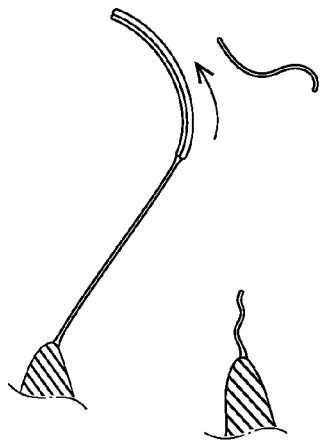
FIGS. 5A and 5B are schematic sectional views of mitral valves with ruptured and elongated chordae, respectively, both causing mitral regurgitation.
Figure 5B:
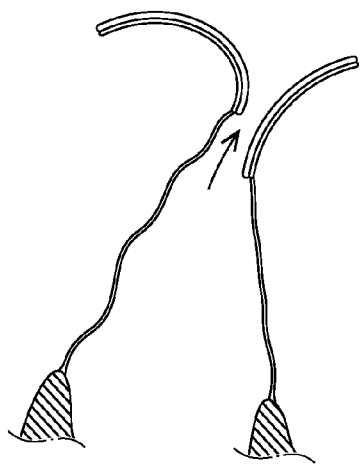
Figure 6A:
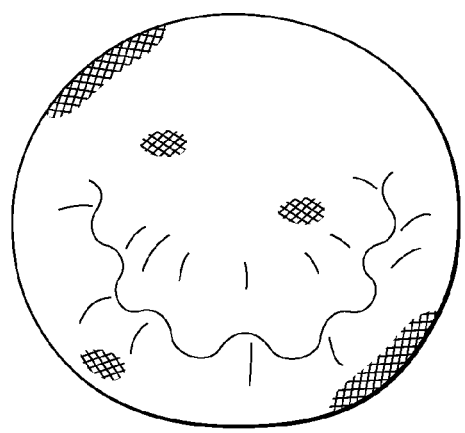
FIGS. 6A and 6B are plan and schematic sectional views of a mitral valve having symptoms of Barlow's disease with excess tissue and irregularly thickened leaflets.
Figure 6B:
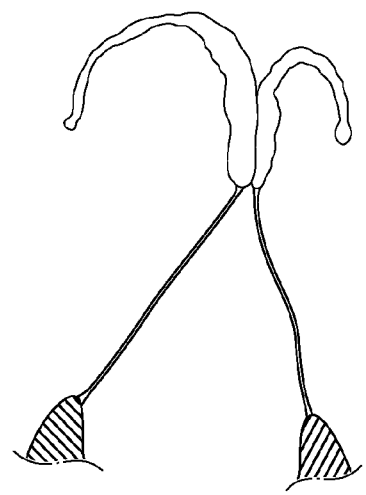
Figure 7A:
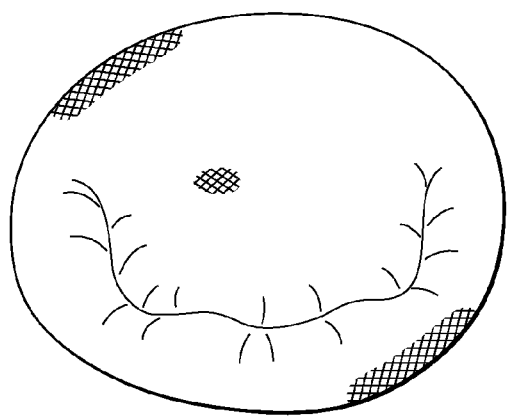
FIGS. 7A and 7B are plan and schematic sectional views of a mitral valve having symptoms of fibro-elastic deficiency with thinned leaflets.
Figure 7B:
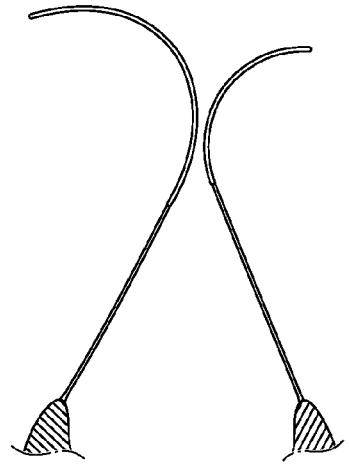
Figure 8A:
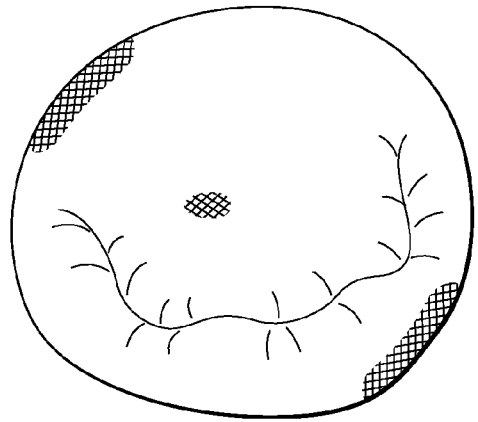
FIGS. 8A and 8B are plan and schematic sectional views of a mitral valve having symptoms of Marfan's disease with excess and thin tissue and elongated chordae.
Figure 8B:
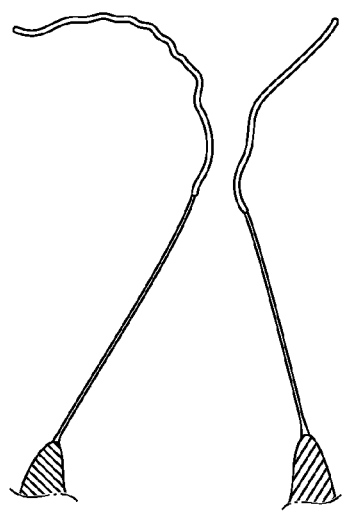
Figure 9A:
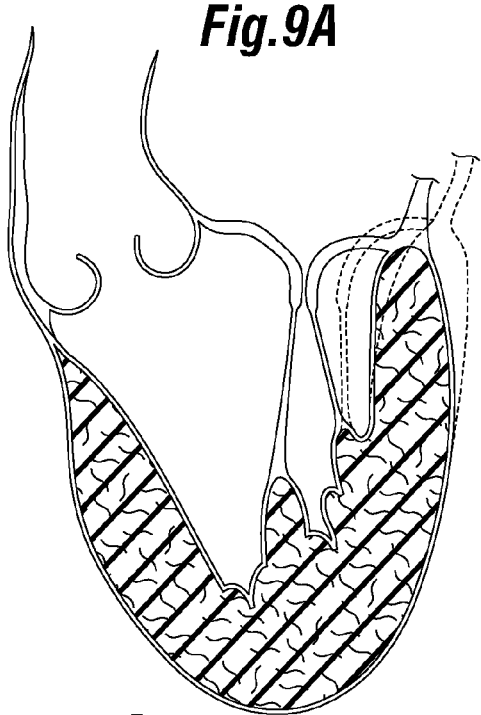
FIGS. 9A-9D illustrate Carpentier's functional classification of mitral regurgitation, namely: Type I—normal leaflet motion, though with annular dilatation; Type II—increased leaflet motion (leaflet prolapse); Type IIIa—restricted leaflet motion in systole; and Type IIIb restricted leaflet motion in diastole.
Figure 9B:
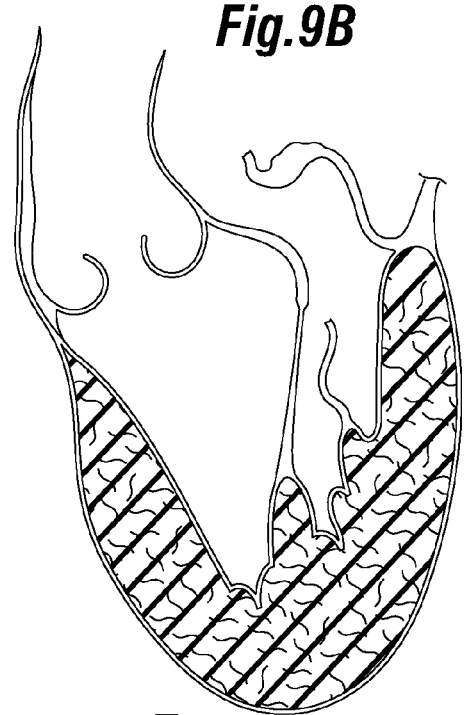
Figure 9C:
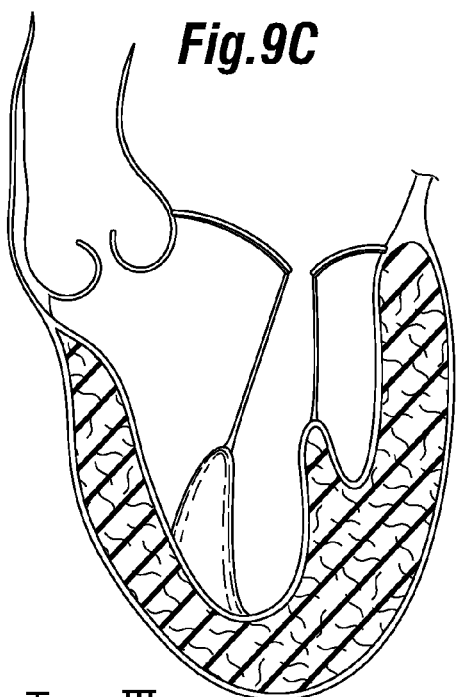
Figure 9D:
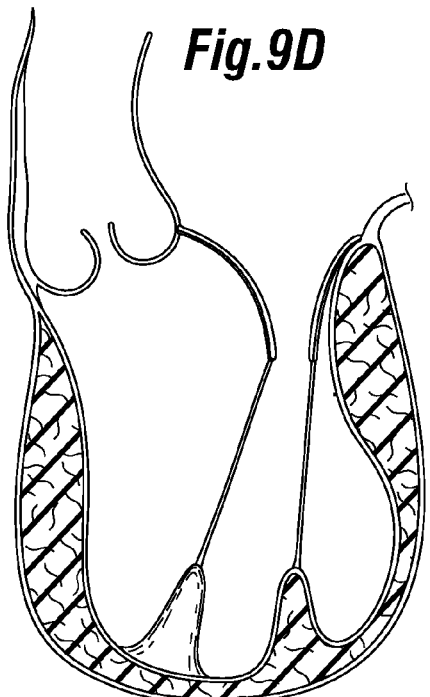

Typical mitral annuloplasty support rings have a long or major dimension and a short or minor dimension, with the conventional ratio of the minor to major dimension being at most 3:4 (75%), and typically less. The annuloplasty rings described here have a gradually increasing minor axis dimension B to major axis dimension A ratio. The dimensions A and B are measured to the inner edge of the body 74. This increasing dimensional ratio provides rings in the larger sizes that are more suited to correcting conditions where the mitral leaflet is floppy, such as the conditions shown in FIGS. 2-4, and in general for Type II pathologies seen in FIG. 9B. Typically, larger patients exhibit this general condition leading to regurgitation as opposed to smaller patients, for which rings having more conventional B/A ratios are more appropriate.

Table II below indicates the approximate values of the major and minor axes as measured across the interior of an exemplary ring body 74 (dimensions A and B, respectively, in FIG. 16A) for nine different exemplary rings, and also gives the ratios of the minor axis to the major axis. Again, these values may vary by ±20%, while maintaining the approximate relative sizes across the ring set. The rings have nominal orifice sizes in even millimeter increments (e.g., 24 mm, 26 mm, etc.) as measured across the major axes. Such rings will have distinct packaging so as to be labeled with the particular size.

TABLE II

| Labeled ring size (mm) | Major axis (mm) | Minor Axis (mm) | B/A ratio |
|---|---|---|---|
| 24 | 24.0 | 16.5 | 0.6875 |
| 26 | 26.0 | 17.7 | 0.6808 |
| 28 | 28.0 | 18.9 | 0.6750 |
| 30 | 30.0 | 20.4 | 0.6800 |
| 32 | 32.0 | 21.9 | 0.6844 |
| 34 | 34.0 | 23.5 | 0.6912 |
| 36 | 36.0 | 25.5 | 0.7083 |

TABLE II-continued

| Labeled ring size (mm) | Major axis (mm) | Minor Axis (mm) | B/A ratio |
|---|---|---|---|
| 38 | 38.0 | 27.2 | 0.7158 |
| 40 | 40.0 | 28.7 | 0.7175 |

To clarify, an exemplary 40 mm ring will have a major axis dimension A of about 40 mm and a minor axis dimension B of about 28.7 mm. The B/A ratio of the larger rings, such as 34 mm or larger, preferably ranges between 0.69 and 0.73, and the approximation "about" encompasses ring sizes within that ratio range. For instance, a 40 mm ring that has a major axis dimension A of exactly 40 mm, may have a minor axis dimension B of between 27.6 mm (0.69×40) and 29.2 mm (0.73×40). Further exemplary dimensions will be provided below for sets of rings in accordance with the present invention. Certain curvatures around the ring in plan view are particularly shaped to correct for degenerative valvular diseases.

Figure 19A:
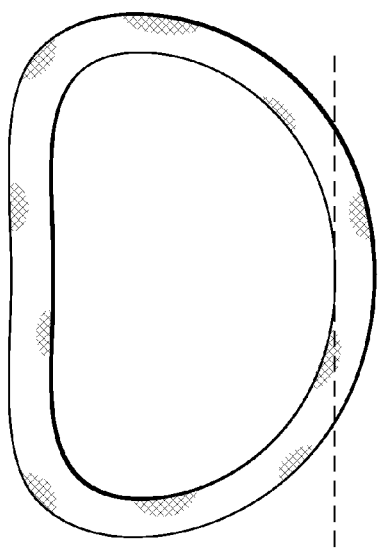
Figure 19B:
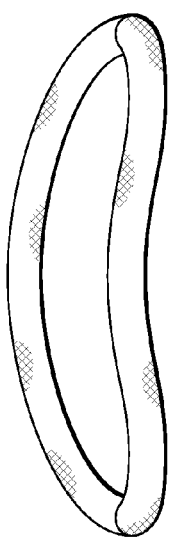
Figure 18A:
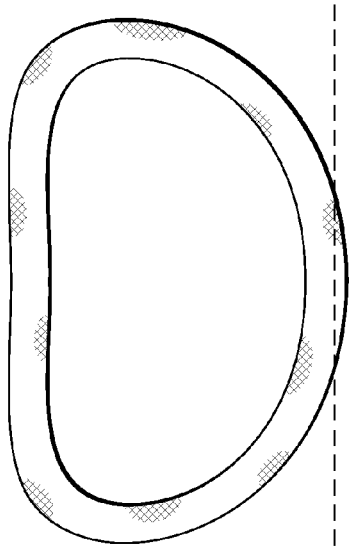
Figure 18B:
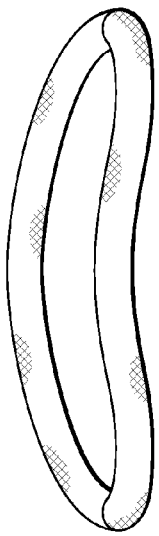
Figure 17A:
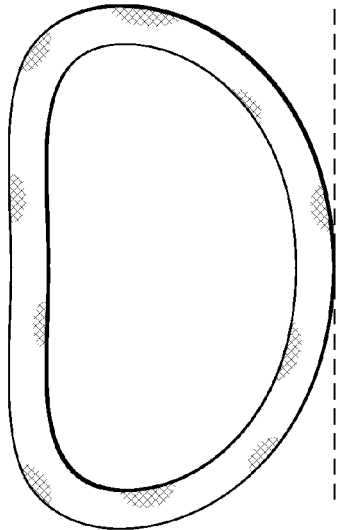
FIGS. 17A/17B, 18A/18B, and 19A/19B show plan and side views of several different sized rings.
Figure 17B:
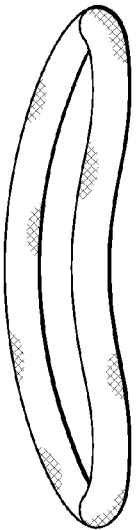

FIGS. 17A-19B show plan and side views of several embodiments of different sized rings for comparison. FIGS. 17A and 17B show a 24 mm ring, FIGS. 18A and 18B show a 32 mm ring, and FIGS. 19A and 19B show a 40 mm ring. The overall "look" of the rings are the same though the B/A ratio increases in the larger rings. That is, the larger rings as in FIG. 19A are more circular to accommodate valves affected by Barlow's disease which typically have a greater orifice size. Indeed, Barlow's, fibro-elastic deficiency, and Marfan's disease all tend to enlarge the orifice of larger annuluses to be more circular. Conversely, the smaller rings as in FIG. 17A have a more pronounced D shape to accommodate valves affected by fibroelastic deficiency, which often affects valves of smaller sizes.

From a surgical point of view, whatever the type of degenerative valvular disease, ring selection can be based on measurement of the intercommissural distance and the height of the anterior leaflet. As mentioned above, the particular shapes of the abnormal annuluses can be obtained from morphometric studies by echocardiography, magnetic resonance imaging (MRI), ultrasound, and direct physical measurements in the operating room. The complex morphology of the degenerative mitral valve renders particularly difficult the selection of the ring. Therefore, in addition to the classic measurements for determining ring size—the intercommissural dimension and the surface area of the anterior leaflet—at least two other measurements may be useful: the height of the anterior leaflet (AL) and the height of the three segments P1, P2, P3 of the posterior leaflet (PL). The antero-posterior diameter of the ring should, preferably, be approximately equivalent to the height of the anterior leaflet measured by appropriate sizers.

Figure 20:
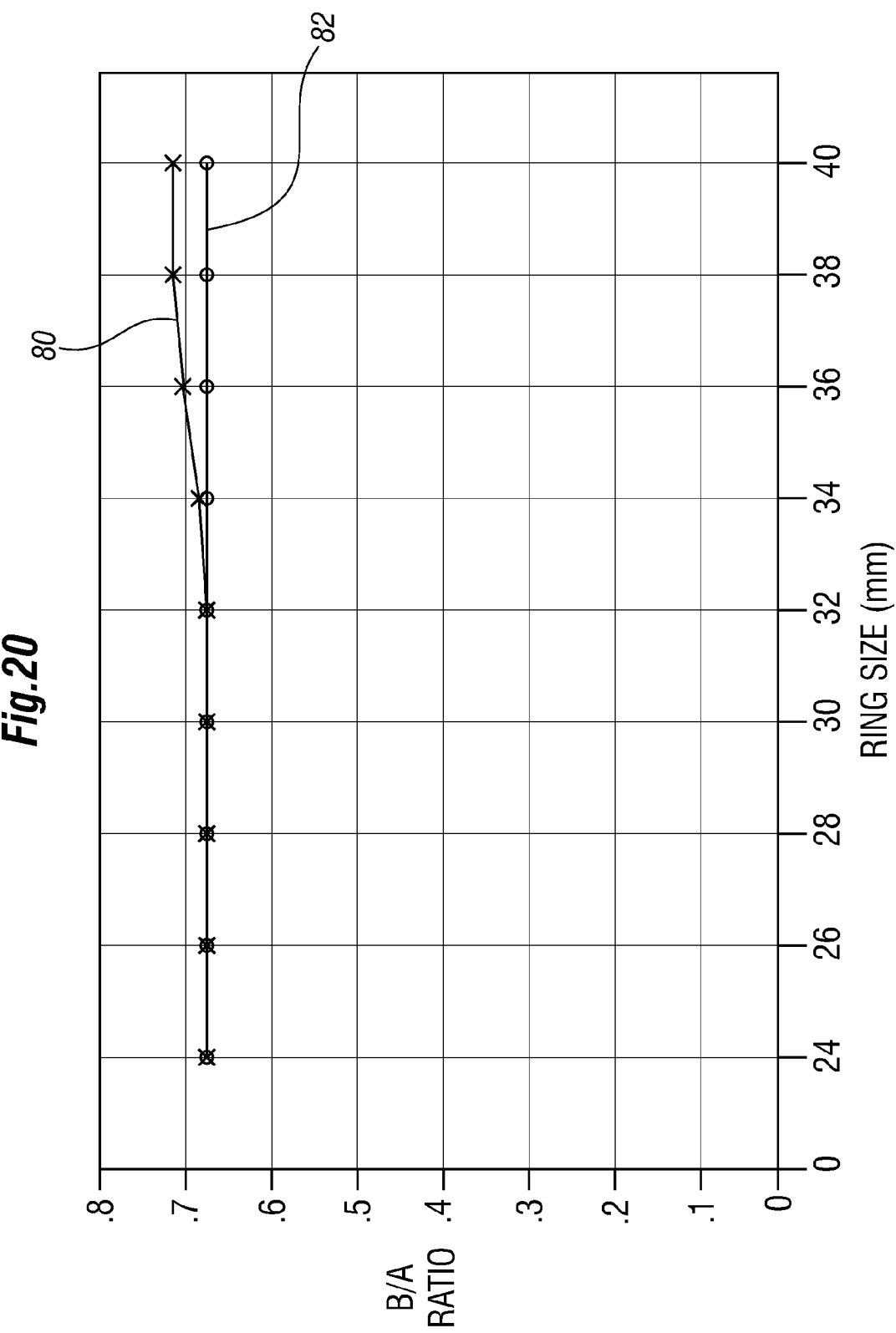
FIG. 20 is a graph showing the changing minor/major axis proportion of the exemplary ring.

FIG. 20 is a graph showing the changing minor/major axis proportion of the exemplary ring along line 80 as compared with a line 82 for a prior art ring, the Carpentier-Edwards Physio® ring. This shows the divergence of the ring proportions starting at around the 32 mm ring. Desirably, the B/A ratio increases at least 10% from the smallest ring to the largest ring, and in the exemplary embodiment B/A increases by about 4% (0.6875/0.7175) from the 24 mm ring to the 40 mm ring.

Figure 21A:
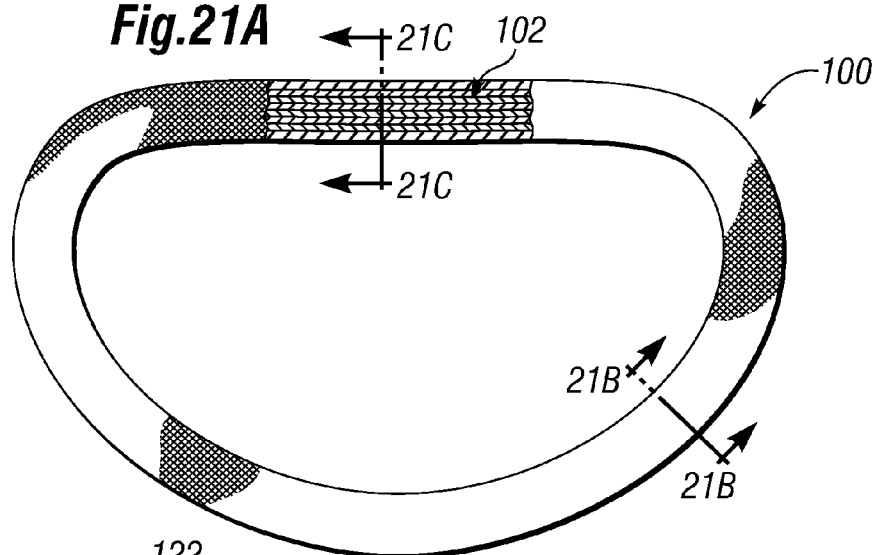
FIGS. 21A-21C show cutaway plan and sectional views of an exemplary ring.
Figure 21B:
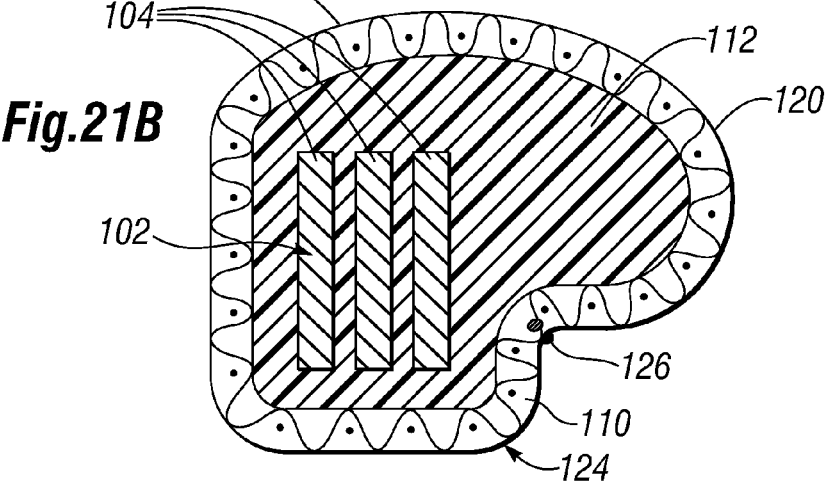
Figure 21C:
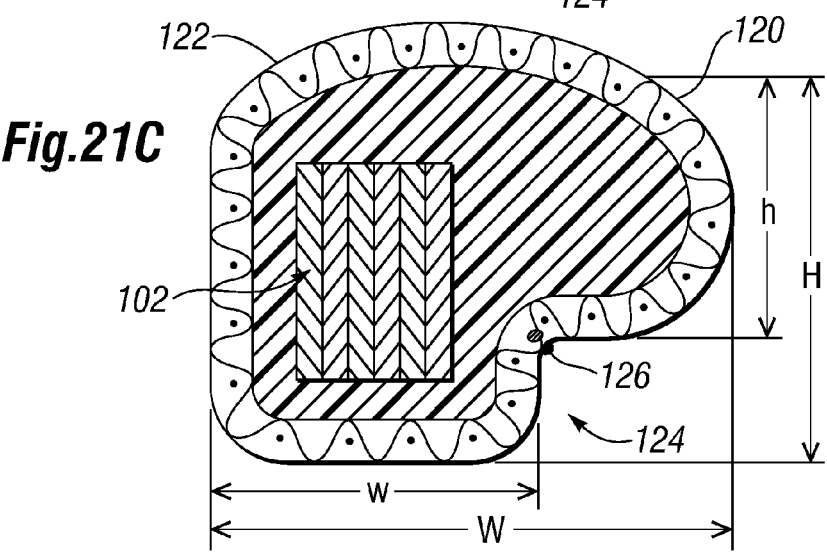

FIGS. 21A-21C show cutaway plan and sectional views showing the construction of an exemplary ring 100 of the present invention. In a preferred embodiment, the annuloplasty ring 100 is defined by a concentric wire band structure 102 resulting in selectively flexibility. Layers are formed by wrapping a single band to form a spiral structure, or by layering individual bands upon one another, with one of such bands shown at 104. Preferably a plurality of individual bands 104 are layered upon one another to form the multi-layered structure 102. The bands 104 are formed from a biocompatible, anti-magnetic material such as Elgiloy®.

This band structure is held within a fabric sheath 110 in a manner similar to the previously described embodiments. The fabric sheath 110 is a knitted structure with optimal tension to avoid irregularities and wrinkles. Marks are typically placed on the fabric to clearly identify the commissures, and a circular mark provided (e.g., with a green suture) to delineate the enhanced sewing cuff. The longitudinal rigidity of the core, the regular contour and optimal profile of the silicone band together with the extreme thinness and optimal stretching of the fabric together comprise a unique combination of structural features which minimizes platelet deposit, fibrous proliferation, and thrombus formation.

Preferably, in order to reduce friction between adjacent bands 104, an elastomeric material such as silicone is placed between the individual band layers, such as seen at 112 in FIG. 17. Selective flexibility is provided by movement of the band leaders separated by the silicone material layers therebetween.

The elastomeric material 112 also surrounds the outside of the band structure 102. As seen in FIGS. 21B and 21C, the fabric sheath 110 bulges outwards along one side, with this bulge or flange, as seen at 120, filled with the elastomeric material 112. This bulge 120 is preferentially positioned along the outside of the ring 100. Sutures will be passed through the bulge 120 which helps prevent them from catching between the bands 104, or otherwise striking the structural core of the ring. The elastic material 112 desirably comprises a molded silicone band that defines the bulge 120. In FIGS. 21B and 21C the upper or inflow side 122 is to the left atrium, while the lower or outflow side 124 is toward the ventricle. The inflow side is thus curved, smooth and streamlined to minimize platelet deposits and fibrous proliferation, while the outflow side has a smooth stepped surface to provide a well identified area for placement of sutures used to secure the ring to the annulus. Desirably, a circular green suture line 126 delineating the underside of the enhanced sewing cuff or bulge 112 also maintains tension in the fabric sheath 110, thus eliminating wrinkles and possible thrombus formation and fibrous proliferation. The green suture line 126 acts as an aid to help facilitate implant of the ring by demarking for the surgeon a boundary on the ring within which sutures should not be passed. The line 126 therefore helps prevent the surgeon from snagging the band structure 102 with an implant suture.

As seen in FIG. 21C, the total axial height H of the exemplary ring 100 is about 3 mm, while the total radial width W is about 3 mm. With such a ring 100, the bulge 120 has a height h of about 50% of the total height H, while the width w of the main portion of the ring is about 70% of the total width W, meaning the bulge 120 has a width of about 30% of the total width W. In the exemplary embodiment, the bulge 120 has an axial height h of about 1.5 mm and a radial width of about 0.8 mm.

The radial cross-sectional profile of the rings is preferably reduced as much as possible to minimize turbulence and adverse consequences such as thrombus formation and fibrous proliferation. Consequently, in the embodiment the maximum cross-section of the wire band structure 102 is limited to about 1.5 mm width and 2.5 mm height, ±10%.

The flexibility of the band structure 102 and thus the ring 100 varies in a direction away from an anterior side. That is, preferably a ratio of the stiffness of the band structure 102, as defined by the bands 104 in the longitudinal direction over the stiffness in the lateral direction is from about 1.15 to about 2.77. In the illustrated embodiment, the band structure 102 includes closely-spaced bands 104 at the anterior side seen in FIG. 21B, with less bands that are also spaced apart around the posterior side, as seen in FIG. 21C. That is, the anterior side of the ring 100 is substantially straighter and more rigid than the posterior side. One way to increase rigidity of the anterior side is to crimp or spot weld the bands together on that side. Similarly, the actual height of the bands may be greater on the anterior side. Desirably, the axial height of the bands ranges between 1.5-2.5 mm. More detail of similar structure and alternatives thereto can be seen in U.S. Pat. No. 5,104,407.

The precise number of band windings forming the body element is dependent upon the materials used for the bands 104, as well as the thickness of the individual band layers forming the multi-layered structure. Generally, from about 1 to about 6 layers or individual bands 104 are used, while the thickness of each layer or band 104 may be from about 0.002 to about 0.008 of an inch.

The use of a layered structure prepared by the overlaying of one or more bands 104 ensures that the force applied against the prosthesis 100 is better distributed over the various layers of the bands. The result is a more even application of load to the entire ring prosthesis 100 in both the longitudinal and lateral directions. Additionally, the layered band structure 102 provides a unique selective flexibility which is predominant in the anterior-posterior (AP) dimension than in the transverse dimension. In other words, the layered band structure 102 has varying degrees of stiffness across different oblique planes as measured by force per unit deflection.

FIGS. 22A-22C illustrate the effects of application of opposite inward forces across different oblique planes on the exemplary rings. The most deformation, and thus the most flexibility in the ring, is seen in FIG. 22A from application of the squeezing force along the antero-posterior plane. The ring is shown in solid line deformed from a dashed outline of the original shape. FIG. 22B illustrates the application of the squeezing force in an oblique plane between the major and minor axes. The ring still deforms, but not quite as much. Finally, FIG. 22C shows the minimum amount of deformation upon application of opposite inward forces generally along the large dimension or major axis of the ring. Because the anterior side (top side in the figures) is more rigid, it limits the amount of bending of the ring from imposition of such a force. Providing maximum stiffness in the transverse plane (along the major axis) ensures adequate remodeling of the valve annulus.

For large ring sizes, which may be more circular as described above, the selective flexibility may be increased to reduce the stress on the degenerative annulus and, therefore, minimize the incidence of ring dehiscence. Thus, the relative flexibility around each ring across a set of rings may differ. Stated generally, rings across a set of differently-sized rings may differ in their proportional size, shape, or physically characteristics such as flexibility. For example, in smaller rings the posterior side may be more flexible than the anterior side, as in the prior art, but for larger ring sizes in the same set of rings the posterior flexibility may be even greater relative to the anterior side. The aforementioned structure can be modified to change the flexibility around the ring. More particularly, the axial height of the bands determines their flexibility at any one point, and thus the height of the bands on the posterior side can be less than on the anterior side for greater flexibility on the posterior side. In relative terms, the axial height of the bands on the posterior side of larger rings may be less than the axial height on the anterior side for smaller rings. At the same time, the axially-oriented band structure provides enough transverse rigidity to avoid complication of the ring.

The stiffness of the rings of the present invention may be calculated as a gram force (gf) required to deflect the ring 1 mm. One exemplary range of stiffness in the antero-posterior direction is about 44.27-75.33 gf/mm, depending on the size of the ring. A 20% variance on this range is contemplated.

The rings described herein can be designed using geometric and mathematical formula. FIGS. 23A-23D and 24 illustrate one exemplary geometric construction of a mitral annuloplasty ring primarily defined by four circular arcs, one for each of the anterior, posterior, and two side segments, and connected at points of tangency.

Figure 23A:
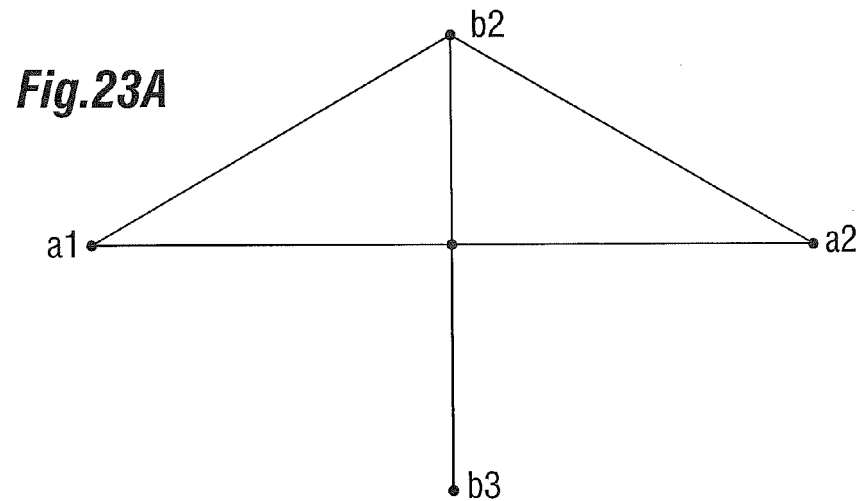
FIGS. 23A-23D illustrate an exemplary sequence of geometric construction of a mitral annuloplasty ring primarily defined by four circular arcs, one for each of the anterior, posterior, and two side segments, and connected at points of tangency.

First, as seen in FIG. 23A, a horizontal line segment a1-a2 is drawn having a length A (see FIG. 24) of the major axis of the ring being constructed. Therefore, for a 40 mm ring, the length A of line segment a1-a2 is 40 mm. The point b1 is located at the center of line segment a1-a2. A vertical line segment b1-b2 is then drawn having a length B' (see FIG. 24) corresponding to the formula:

$$B'=(0.3125 \cdot A)-0.8 \text{(all dimensions in mm)}$$

Still with reference to FIG. 23A, congruent triangles b1-b2-a1 and b1-b2-a2 are completed by drawing the hypotenuses along line segments b2-a1 and b2-a2. The point b3 is located by extending the vertical line segment b1-b2 downward so that the length B (see FIG. 24) of line segment b2-b3 corresponds to the value shown in table II for the corresponding ring size A.

Figure 23B:
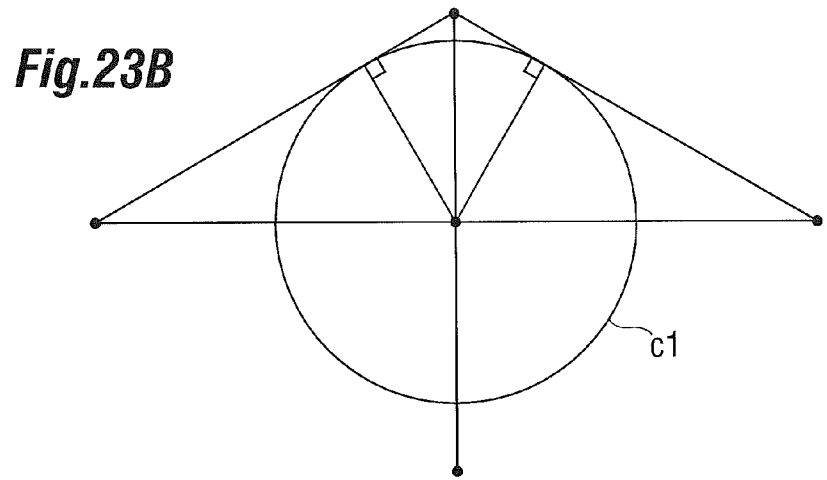
Figure 23C:
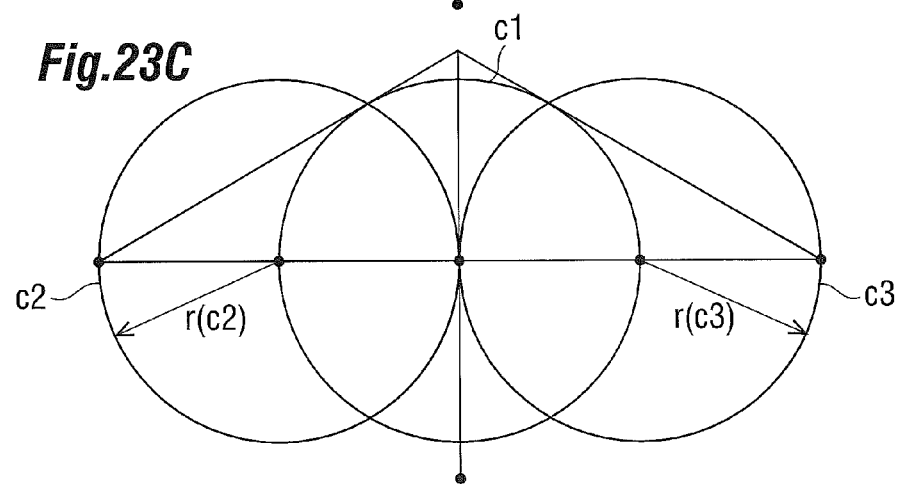

FIG. 23B shows a central circle c1 drawn with its center on point b1 and having a radius that extends orthogonally to the two hypotenuses extending along line segments b2-a1 and b2-a2. Another way to look at this is that circle c1 is tangent to both line segments b2-a1 and b2-a2. Next, FIG. 23C shows the construction of identical side circles c2 and c3. Side circle c2 includes points a1 and b1, while side circle c3 includes points a2 and b1. The three circles c1, c2, c3 thus divide line segment a1-a2 into four equal segments with at least one half-circle extending along each segment. Another way to state this is that circles c1, c2, c3 are congruent circles whose centers are equidistantly spaced along the major axis line segment a1-a2. Also, the two outer circles c2, c3 include points a1 and a2, respectively, and both including center point b1.

Figure 23D:
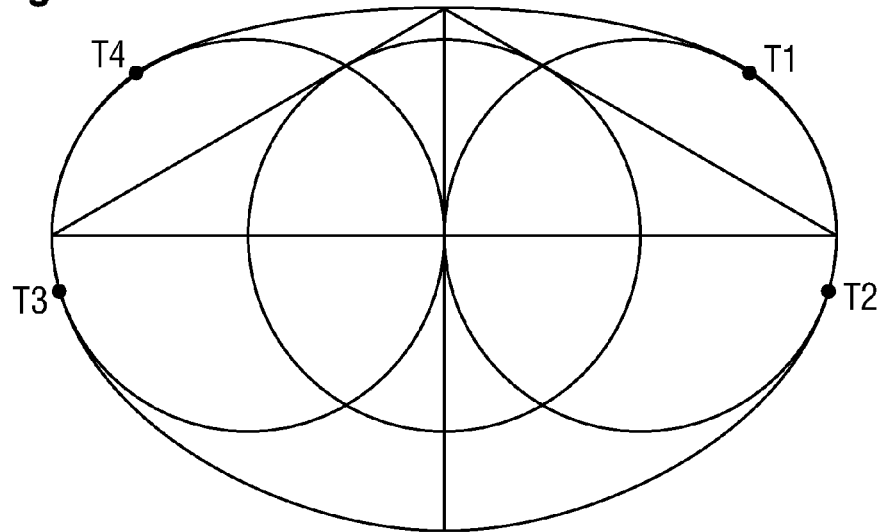

Now with reference to FIG. 23D, large arcs T1-T4 and T2-T3 are drawn across the top and bottom of the geometric form, respectively. Each of these arcs is tangent at both ends to the side circles c2 and c3 and includes, respectively, points b2 and b3. That is, arc T1-T4 is tangent at both ends to the outer circles c2 and c3 and includes point b2, and arc T2-T3 is tangent at both ends to the outer circles c2 and c3 and includes point b3.

Figure 24:
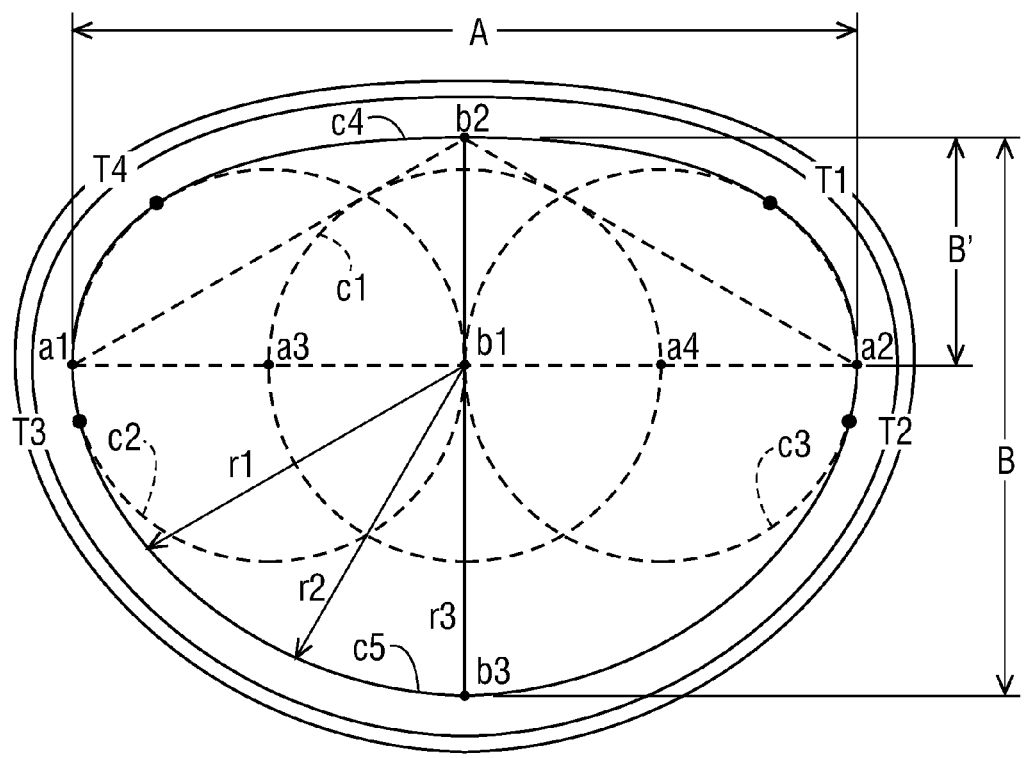
FIG. 24 illustrates a completed exemplary geometric construction of a mitral annuloplasty ring showing primary dimensions.

As seen in FIG. 24, the geometric shape thus formed provides an outline for the inner dimension of each of the rings in the exemplary set of rings. Specifically, the geometric shape is formed at the sides by arcs T1-T2 and T3-T4 along circles c2 and c3, and at the top and bottom by the large arcs T1-T4 and T2-T3 that are tangent to those circles. The final annuloplasty ring periphery is defined by the four circular arcs T1-T2 and T3-T4, and T1-T4 and T2-T3.

FIG. 24 also illustrates several dimensions r1, r2, r3 from the central point b1 to the posterior side of the ring. Although these dimensions appear as radii, each is not technically a radius but instead an oblique dimension extending from the geometric central point b1 of the ring towards the posterior segment of the ring. Because the arc T2-T3 drawn on the posterior side is not centered at b1, the dimensions r1, r2, r3 differ. Desirably, a ring of the present invention is constructed taking into account a number of measurements of an annulus characteristic of the disease that afflicts the valve being treated, including at least 3, and preferably 5, oblique dimensions extending from the geometric center of the annulus to the posterior aspect of the annulus. Following the ring design methods described herein will result in a ring for each size that has similar if not identical oblique dimensions, as shown at r1, r2, r3 in FIG. 24.

Table III below provides values for some of the dimensions illustrated in FIG. 24. The major axis dimensions A and B have been listed above in Table II, while the anterior and posterior heights of the exemplary ring were provided in Table I.

TABLE III

| Labeled ring size (mm) | B' (mm) | r1 (mm) | r2 (mm) | r3 (mm) |
|---|---|---|---|---|
| 24 | 6.7 | 10.8 | 10.1 | 9.8 |
| 26 | 7.3 | 11.8 | 10.7 | 10.4 |
| 28 | 7.9 | 12.7 | 11.4 | 10.9 |
| 30 | 8.6 | 13.8 | 12.3 | 11.8 |
| 32 | 9.2 | 14.9 | 13.2 | 12.7 |
| 34 | 9.8 | 16.0 | 14.3 | 13.7 |
| 36 | 10.4 | 17.3 | 15.6 | 15.1 |
| 38 | 11.1 | 18.9 | 17.0 | 16.1 |
| 40 | 11.7 | 19.1 | 17.9 | 17.5 |

Figure 25C:
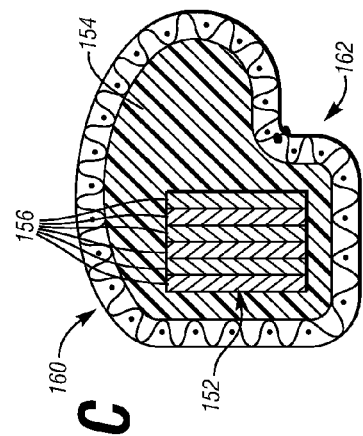
FIGS. 25A-25C are several views of an alternative annuloplasty ring having an inner ring body and an outer suture-permeable cover.
Figure 25A:
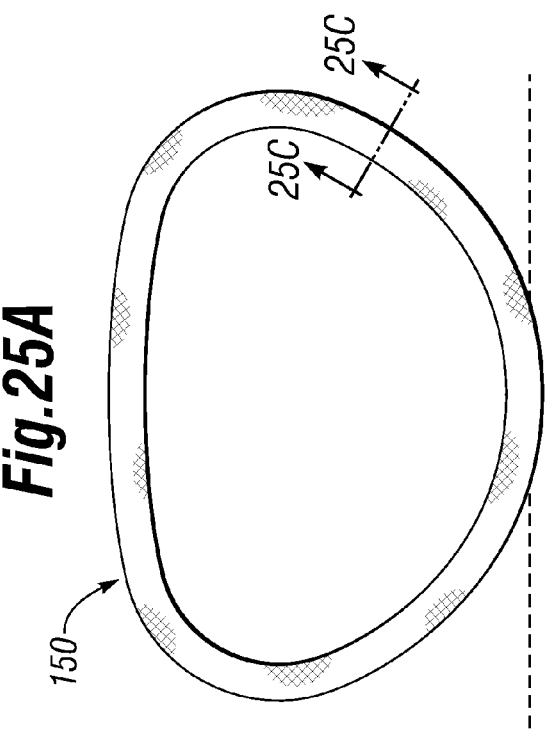
Figure 25B:
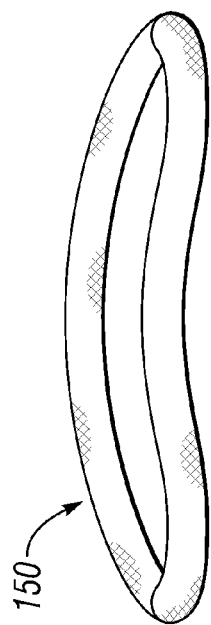

FIGS. 25A-25C are several views of an alternative annuloplasty ring 150 having an inner ring body 152 and an outer suture-permeable cover 154. The inner ring body 152 comprises a series of concentric bands 156, as described above. The cross-section of the ring 150 in FIG. 25C is desirably the same as described above, with an inflow side 160 that is curved, smooth and streamlined to minimize platelet deposits and fibrous proliferation, and an outflow side 162 with a smooth stepped surface to provide a well identified area for placement of sutures used to secure the ring to the annulus.

Figure 26:
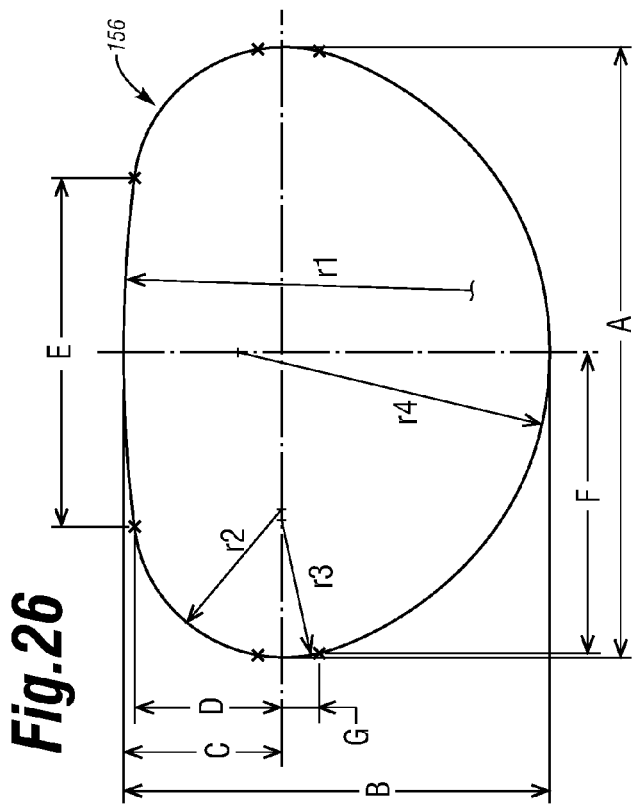
FIG. 26 is a plan view of the inner dimension of the ring body of the alternative ring of FIGS. 25A-25C.

FIG. 26 is a plan view of an inner band 156 of the ring body 152 of FIGS. 25A-25C. The concentric bands radiate outward from the inner band, and are generally proportionally congruent. Four different radii $r_1$, $r_2$, $r_3$, and $r_4$ are indicated around the periphery, meaning there are six (6) different circular arc segments around the ring periphery (arcs with radii $r_2$ and $r_3$ being on both sides). In contrast to the earlier embodiment, however, some of the radii are centered off the minor axis. In an exemplary embodiment, the inner band 156 is for a 24 mm ring and the dimensions in mm are: A=24.0, B=16.6, C=6.0, D=5.7, E=13.6, F=11.80, G=1.5, $r_1$=66.04, $r_2$=12.24, $r_3$=5.77 and $r_4$=5.54. The small crosses (x) around the band periphery mark the boundary between arc segments, and the dimensions D, F and G indicate locations of those boundaries.

Table IV below indicates the approximate values of the major and minor axes (A, B) of the exemplary inner band 156 of the ring body 152 of FIGS. 25A-25C, as well as exemplary dimensions and curvatures, for nine different exemplary rings. As stated above for other embodiments, these values may vary while maintaining the approximate relative sizes across the ring set. The rings have orifice sizes in even millimeter increments (e.g., 24 mm, 26 mm, etc.) as measured across the major axes.

TABLE IV

| Ring size (mm) | A (mm) | B (mm) | B/A ratio | $r_1$ (inch) | $r_2$ (inch) | $r_3$ (inch) | $r_4$ (inch) |
|---|---|---|---|---|---|---|---|
| 24 | 24.0 | 16.5 | 0.6875 | 2.60 | 0.23 | 0.22 | 0.48 |
| 26 | 26.0 | 17.7 | 0.6808 | 2.58 | 0.25 | 0.27 | 0.54 |
| 28 | 28.0 | 18.9 | 0.6750 | 2.55 | 0.27 | 0.32 | 0.61 |
| 30 | 30.0 | 20.4 | 0.6800 | 2.53 | 0.28 | 0.37 | 0.66 |
| 32 | 32.0 | 21.9 | 0.6844 | 2.50 | 0.30 | 0.42 | 0.73 |
| 34 | 34.0 | 23.5 | 0.6912 | 2.40 | 0.35 | 0.47 | 0.79 |
| 36 | 36.0 | 25.5 | 0.7083 | 2.30 | 0.40 | 0.49 | 0.82 |
| 38 | 38.0 | 27.2 | 0.7158 | 2.20 | 0.45 | 0.52 | 1.03 |
| 40 | 40.0 | 29.2 | 0.7300 | 2.10 | 0.38 | 0.59 | 0.83 |

While the invention has been described in its preferred embodiments, it is to be understood that the words which have been used are words of description and not of limitation. Therefore, changes may be made within the appended claims without departing from the true scope of the invention.

What is claimed is:

1. A set of mitral annuloplasty rings for correcting a mitral heart valve annulus from which one can be selected for implant, the set of mitral annuloplasty rings comprising:
a set of rings, each ring having a ring body able to resist deformation when subjected to a stress imparted thereon by a mitral valve annulus and arranged around a flow axis having an upward direction and a downward direction, the downward direction corresponding to the direction of blood flow through the mitral valve annulus when the annuloplasty ring is implanted, each ring body in plan view defining, as measured to the inner edge of the ring body, a major axis A extending across the widest point on the ring body and a minor axis B extending across from an anterior segment to a posterior segment perpendicular to the major axis A, and each ring having an identified orifice size; and
wherein proportional shapes of the ring bodies are different for different identified orifice sizes to comply with predicted shapes of a particular degenerative valvular disease for different annulus orifice sizes, wherein the ring bodies are three-dimensional with opposite sides of each ring body curving upward above a datum plane to a respective height, and wherein the different proportional shapes of the ring bodies comprises differences in the ratio of the heights of the opposite sides, and wherein,
each ring further includes a suture-permeable covering over the ring body.

2. The set of mitral annuloplasty rings of claim 1, wherein a center of the anterior segment rises to a height C and a center of the posterior segment rises to height D above a common datum plane, wherein the ratio C/D>1.

3. The set of mitral annuloplasty rings of claim 2, wherein the ratio C/D is about 3:1.

4. The set of mitral annuloplasty rings of claim 2, wherein the height C of the anterior segment rises up to at least 6 mm above the common datum plane.

5. The set of mitral annuloplasty rings of 1, wherein the predicted shapes of the particular degenerative valvular disease have been calculated from echocardiographic and intraoperative measurements.

6. The set of mitral annuloplasty rings of claim 5, wherein the echocardiographic and intraoperative measurements include transverse diameter, antero-posterior diameter, and at least three oblique dimensions extending from the geometric center of the annulus to the posterior aspect of the annulus.

7. The set of mitral annuloplasty rings of claim 1, wherein the plan view shape of the ring bodies is different for different identified orifice sizes, with a smallest ring within the set having a pronounced D-shape and each ring body for orifice sizes above 32 mm has a successively less pronounced D-shape and becomes more circular than the shape of the ring body for the next smaller identified orifice size.

8. The set of mitral annuloplasty rings of claim 1, wherein the ratio B/A for each ring body changes with increasing ring orifice size.

9. The set of mitral annuloplasty rings of claim 1, wherein a center of the anterior segment rises to a height C and a center of the posterior segment rising to height D above the datum plane, and wherein the differences in the ratio of the heights of the opposite sides comprises different C/D ratios.

10. The set of mitral annuloplasty rings of claim 1, wherein each ring body has varying flexibility around its periphery, and wherein the relative flexibility between the anterior segment and the posterior segment for the respective ring bodies is different with increasing ring orifice size.

11. The set of mitral annuloplasty rings of claim 1, wherein a stepped outflow side of each suture-permeable covering defines an outward bulge and includes a circular green suture line delineating an underside of the bulge.

12. The set of mitral annuloplasty rings of claim 1, wherein the covering has a stepped outflow side.

13. A set of mitral annuloplasty rings for correcting a mitral heart valve annulus from which one can be selected for implant, the set of mitral annuloplasty rings comprising:
a set of rings, each ring having a ring body able to resist deformation when subjected to a stress imparted thereon by a mitral valve annulus and arranged around a flow axis having an upward direction and a downward direction, the downward direction corresponding to the direction of blood flow through the mitral valve annulus when the annuloplasty ring is implanted, each ring body in plan view defining, as measured to the inner edge of the ring body, a major axis A extending across the widest point on the ring body and a minor axis B extending across from an anterior segment to a posterior segment perpendicular to the major axis A, and each ring having an identified orifice size; and
wherein proportional shapes of the ring bodies are different for different identified orifice sizes to comply with predicted shapes of a particular degenerative valvular disease for different annulus orifice sizes, wherein each ring body has varying flexibility around its periphery, and wherein the relative flexibility between the anterior segment and the posterior segment for the respective ring bodies is different with increasing ring orifice size, and wherein,
each ring further includes a suture-permeable covering over the ring body.

14. The set of mitral annuloplasty rings of claim 13, wherein a center of the anterior segment rises to a height C and a center of the posterior segment rises to height D above a common datum plane, wherein the ratio C/D>1.

15. The set of mitral annuloplasty rings of claim 14, wherein the ratio C/D is about 3:1.

16. The set of mitral annuloplasty rings of claim 13, wherein the predicted shapes of the particular degenerative valvular disease have been calculated from echocardiographic and intraoperative measurements.

17. The set of mitral annuloplasty rings of claim 13, wherein the plan view shape of the ring bodies is different for different identified orifice sizes, with a smallest ring within the set having a pronounced D-shape and each ring body for orifice sizes above 32 mm has a successively less pronounced D-shape and becomes more circular than the shape of the ring body for the next smaller identified orifice size.

18. The set of mitral annuloplasty rings of claim 13, wherein the ratio B/A for each ring body changes with increasing ring orifice size.

19. The set of mitral annuloplasty rings of claim 13, wherein a stepped outflow side of each suture-permeable covering defines an outward bulge and includes a circular green suture line delineating an underside of the bulge.

20. A set of mitral annuloplasty rings for correcting a mitral heart valve annulus from which one can be selected for implant, the set of mitral annuloplasty rings comprising:
a set of rings, each ring having a ring body able to resist deformation when subjected to a stress imparted thereon by a mitral valve annulus and arranged around a flow axis having an upward direction and a downward direction, the downward direction corresponding to a direction of blood flow through the mitral valve annulus when the annuloplasty ring is implanted, each ring body in plan view defining, as measured to the inner edge of the ring body, a major axis A extending across the widest point on the ring body and a minor axis B extending across from an anterior segment to a posterior segment perpendicular to the major axis A, and each ring having an identified orifice size;
wherein a ratio B/A for each ring body changes with increasing ring orifice size;
wherein the ring bodies are three-dimensional with a center of the anterior segment curving upward to a height C and a center of the posterior segment curving upward to a height D above a common datum plane, and wherein a ratio C/D for each ring body is different with increasing ring orifice size; and
each ring further includes a suture-permeable covering over the ring body.

21. The set of mitral annuloplasty rings of claim 20, wherein the ring bodies are generally D-shaped in plan view, and wherein the shape of the ring bodies is different for different identified orifice sizes, with a smallest ring within the set having a pronounced D-shape and each ring body for orifice sizes above 32 mm has a successively less pronounced D-shape and becomes more circular than the shape of the ring body for the next smaller identified orifice size.

22. The set of mitral annuloplasty rings of claim 20, wherein the ratio C/D for each ring body is different with increasing ring orifice size and the height C of the anterior segment rises up to at least 6 mm above the common datum plane in at least one of the rings.

23. The set of mitral annuloplasty rings of claim 20, wherein the covering has a stepped outflow side.

24. The set of mitral annuloplasty rings of claim 20, wherein the ring bodies each define a continuous periphery.

25. The set of mitral annuloplasty rings of claim 20, wherein each ring body has varying flexibility around its periphery, and wherein the relative flexibility between the anterior segment and the posterior segment for the respective ring bodies is different with increasing ring orifice size.

26. The set of mitral annuloplasty rings of claim 20, wherein a stepped outflow side of each suture-permeable covering defines an outward bulge and includes a circular green suture line delineating an underside of the bulge.

27. The set of mitral annuloplasty rings of claim 20, wherein the ratio B/A for each ring body is larger only for orifice sizes above 32 mm.

* * * * *